US010299762B2

(12) United States Patent
Yamamoto

(10) Patent No.: US 10,299,762 B2
(45) Date of Patent: May 28, 2019

(54) ULTRASOUND DIAGNOSTIC APPARATUS, SIGNAL PROCESSING METHOD FOR ULTRASOUND DIAGNOSTIC APPARATUS, AND RECORDING MEDIUM

(71) Applicant: FUJIFILM Corporation, Tokyo (JP)

(72) Inventor: Hiroaki Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 930 days.

(21) Appl. No.: 14/849,940

(22) Filed: Sep. 10, 2015

(65) Prior Publication Data

US 2015/0374339 A1    Dec. 31, 2015

Related U.S. Application Data

(63) Continuation of application No. PCT/JP2014/052872, filed on Feb. 7, 2014.

(30) Foreign Application Priority Data

Mar. 22, 2013    (JP) .................................. 2013-060104

(51) Int. Cl.
| | | |
|---|---|---|
| *A61B 8/08* | (2006.01) | |
| *A61B 8/14* | (2006.01) | |
| *A61B 8/00* | (2006.01) | |
| *G01S 7/52* | (2006.01) | |
| *G01S 15/89* | (2006.01) | |

(52) U.S. Cl.
CPC .......... *A61B 8/5207* (2013.01); *A61B 8/4483* (2013.01); *A61B 8/54* (2013.01); *G01S 7/52046* (2013.01); *G01S 15/8915* (2013.01); *A61B 8/145* (2013.01)

(58) Field of Classification Search
CPC ..... A61B 8/145; A61B 8/4483; A61B 8/5207; A61B 8/54; G01S 15/8915; G01S 7/52046
See application file for complete search history.

(56) References Cited

U.S. PATENT DOCUMENTS

| | | | |
|---|---|---|---|
| 2009/0326377 A1 | 12/2009 | Hirama | |
| 2016/0007971 A1* | 1/2016 | Yamamoto ........... | A61B 8/5207 600/447 |

FOREIGN PATENT DOCUMENTS

| | | | |
|---|---|---|---|
| JP | 2004195091 A | * | 7/2004 |
| JP | 2009-240700 A | | 10/2009 |

OTHER PUBLICATIONS

International Search Report issued in PCT/JP2014/052872, dated Mar. 4, 2014.

(Continued)

*Primary Examiner* — Michael T Rozanski
(74) *Attorney, Agent, or Firm* — Birch, Stewart, Kolasch & Birch, LLP

(57) ABSTRACT

An object of the present invention is to provide an ultrasound diagnostic apparatus, a signal processing method, and a recording medium which are capable of eliminating a ghost signal with a small number of data when correcting element data by superimposing a plurality of element data, obtaining a high quality ultrasound image while preventing a decrease in the frame rate, and reducing the capacity of a memory. Information on a transmission frequency of an ultrasonic beam is acquired, and second element data is generated using a plurality of first element data on the basis of the acquired information on a transmission frequency.

10 Claims, 15 Drawing Sheets

(56) References Cited

OTHER PUBLICATIONS

English translation of the International Preliminary Report on Patentability and Written Opinion of the International Searching Authority (Forms PCT/IB/338, PCT/IB/373 and PCT/ISA/237), dated Oct. 1, 2015, for International Application No. PCT/JP2014/052872.

* cited by examiner

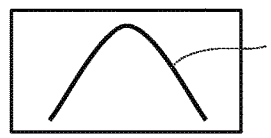
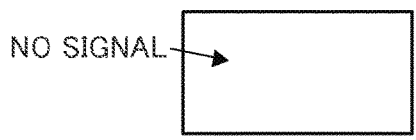
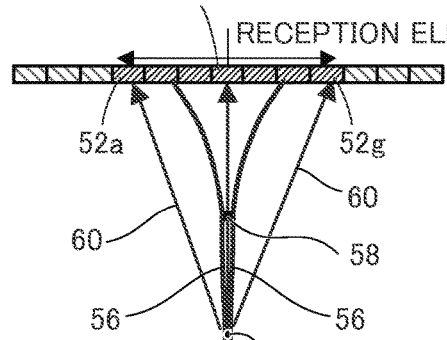
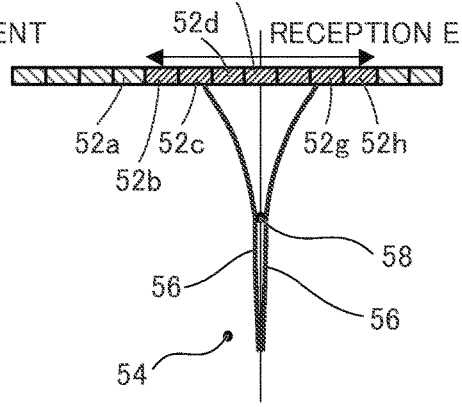
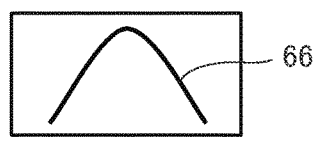
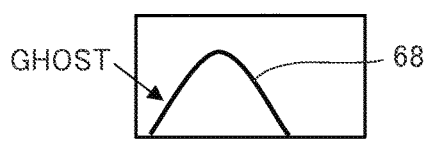
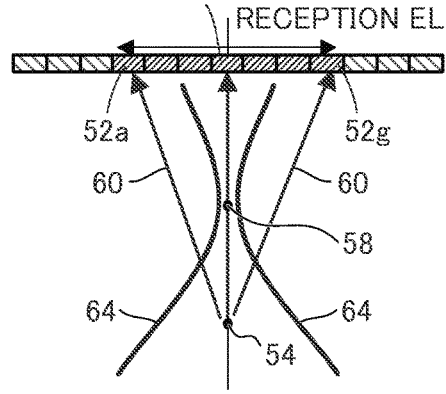
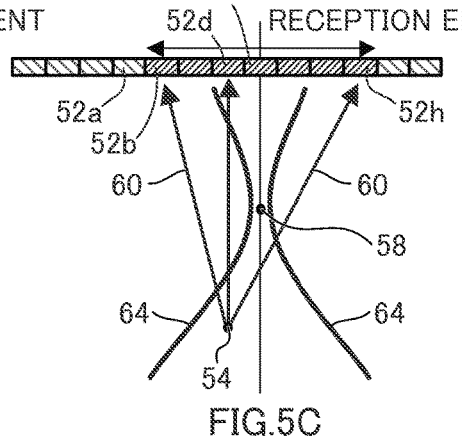

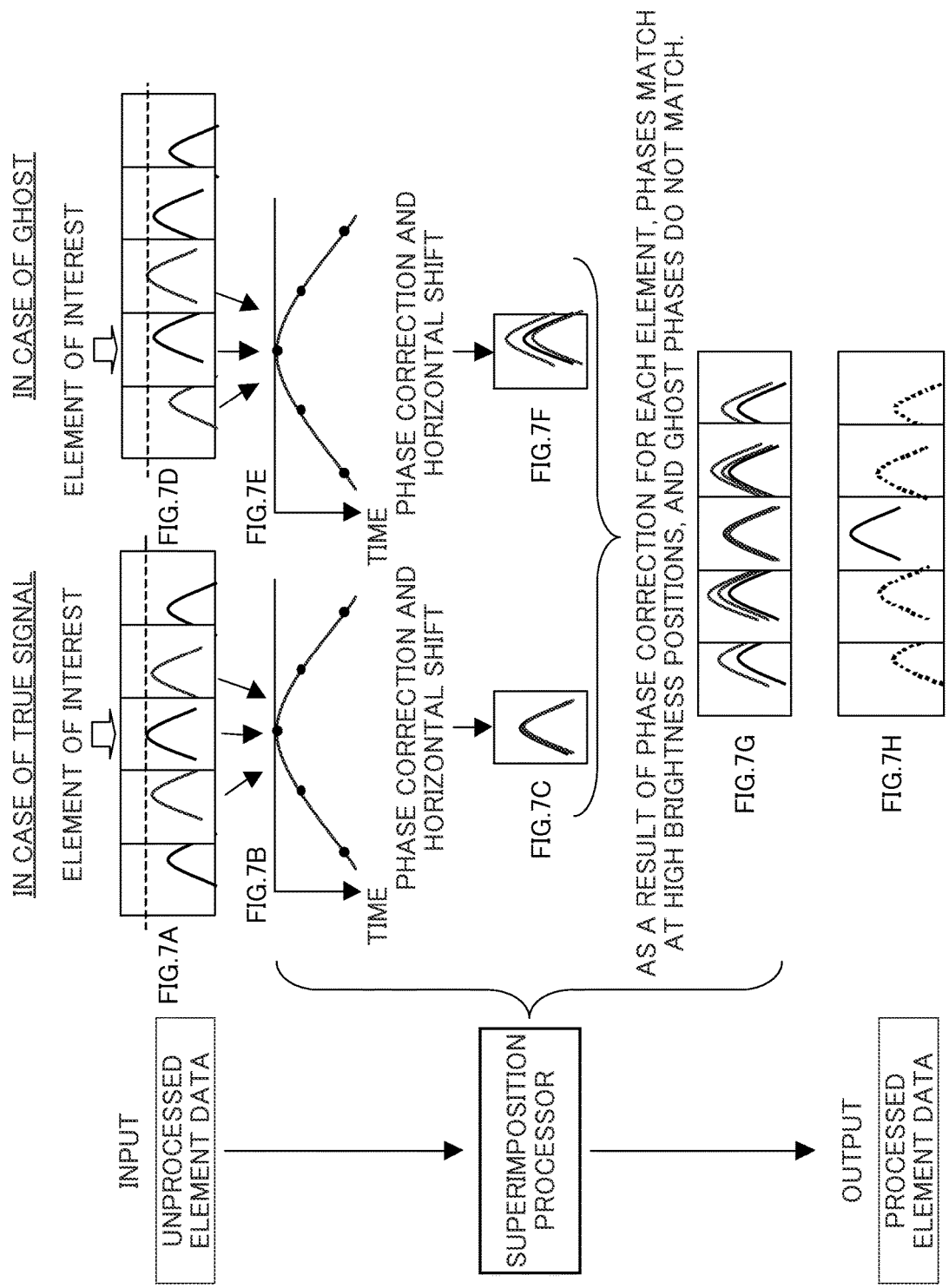

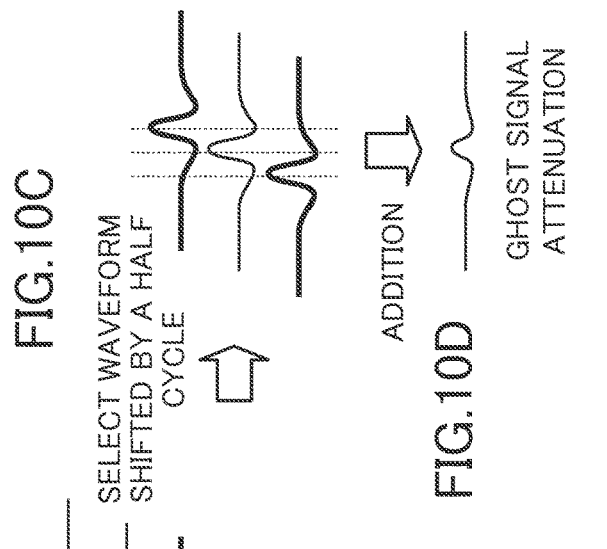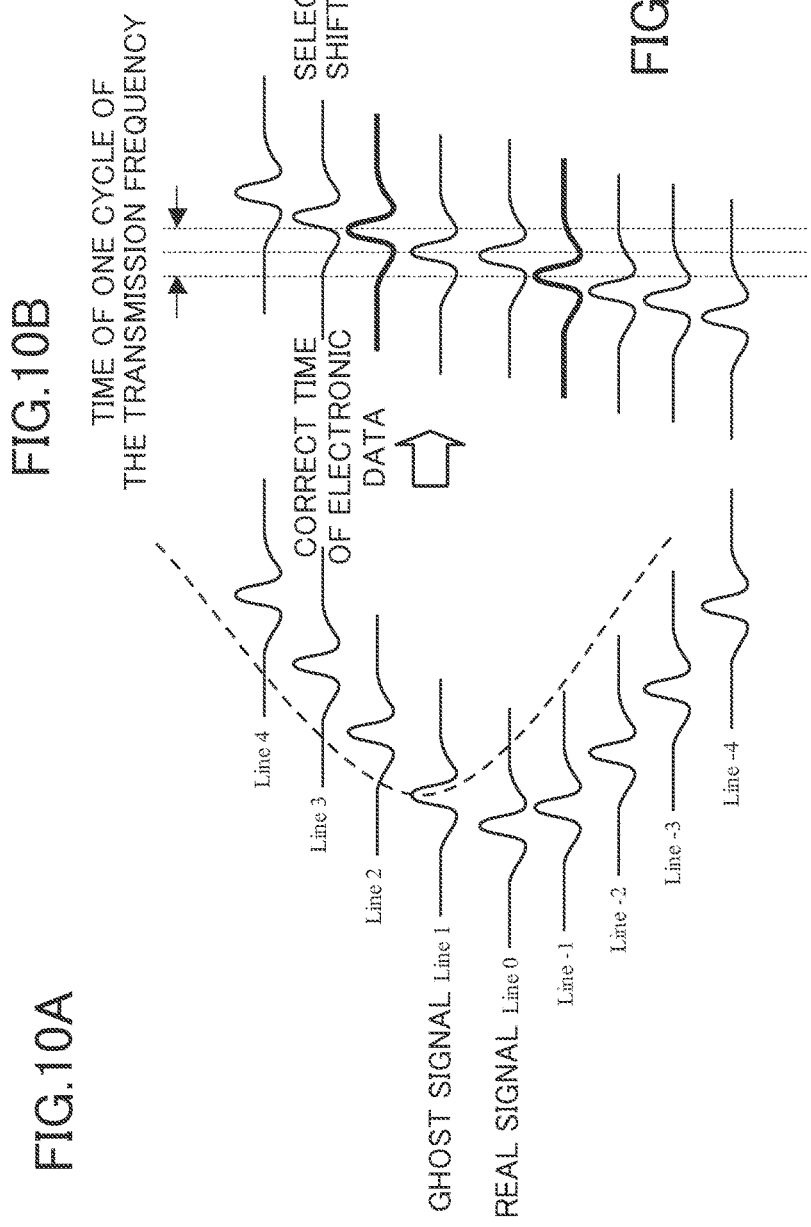

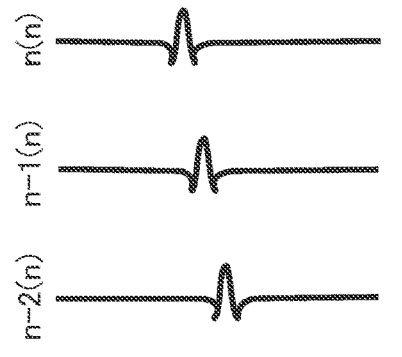
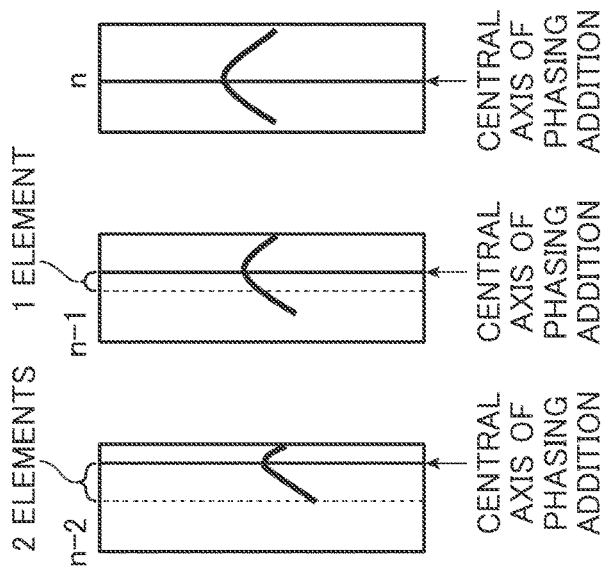

ULTRASOUND DIAGNOSTIC APPARATUS, SIGNAL PROCESSING METHOD FOR ULTRASOUND DIAGNOSTIC APPARATUS, AND RECORDING MEDIUM

CROSS-REFERENCE TO RELATED APPLICATIONS

This application is a Continuation of PCT International Application No. PCT/JP2014/052872 filed on Feb. 7, 2014, which claims priority under 35 U.S.C. § 119(a) to Japanese Patent Application No. 2013-060104 filed on Mar. 22, 2013. The above application is hereby expressly incorporated by reference, in its entirety, into the present application.

BACKGROUND OF THE INVENTION

The present invention relates to an ultrasound diagnostic apparatus for taking an image of an inspection object such as an organ in a living body by transmitting and receiving an ultrasonic beam to generate an ultrasound image used for inspection and diagnosis of the inspection object, a signal processing method, and a recording medium.

Conventionally, ultrasound diagnostic apparatuses such as ultrasound image diagnostic apparatuses using ultrasound images are put to practical use in the medical field.

Generally, this type of ultrasound diagnostic apparatus includes an ultrasound probe (hereinafter, referred to as "probe") with a plurality of built-in elements (ultrasound transducers) and an apparatus main body connected with the probe. In the ultrasound diagnostic apparatus, an ultrasonic beam is transmitted from the plurality of elements of the probe toward a subject (an inspection object) so as to form a predetermined focus point (transmission focus point), an ultrasonic echo from the subject is received by the probe, and an ultrasound image is generated by electrically processing the reception signal of the received ultrasonic echo in the apparatus main body.

In the meantime, the ultrasonic beam is transmitted by the plurality of elements being driven on the basis of a predetermined transmission delay pattern so as to form a set focus point. Such an ultrasonic beam is shaped to be wide in the lateral direction. Therefore, there is a problem in that information on a reflection point located at a position shifted in the lateral direction is picked up and reproduced on the ultrasound image as so-called a ghost signal.

To solve such a problem, in formation of one ultrasound image, the ultrasound diagnostic apparatus superimposes a plurality of data (element data or reception data) obtained by each transmission according to reception times or positions of the elements to correct the data, which is so-called multi-line processing (JP 2009-240700 A). For the ghost signals, even when data is superimposed according to the reception time or the position of the elements, it is possible to eliminate the ghost signals because the ghost signals are superimposed in a shifted state and cancel each other out.

SUMMARY OF THE INVENTION

Here, in the ultrasound diagnostic apparatus that performs such multi-line processing, there is a case in which the ghost signals cannot sufficiently be eliminated when the number of data to be superimposed in the multi-line processing is small. In addition, while the effect of the multi-line processing can be effectively obtained to reliably eliminate the ghost signals when the number of data to be superimposed is large, the signal processing takes time. Therefore, there is a problem in that this leads to a decrease in the frame rate.

In addition, there is a problem in that a large capacity memory is necessary in order to temporarily hold (store) a large number of signals and thus costs are increased.

To solve the problems of the conventional techniques, an object of the present invention is to provide an ultrasound diagnostic apparatus, a signal processing method, and a recording medium which are capable of eliminating a ghost signal with a small number of data when correcting data by superimposing a plurality of data obtained by different instances of transmission and reception in order to generate one ultrasound image, obtaining a high quality ultrasound image while preventing a decrease in the frame rate, and preventing increases in costs without increasing the capacity of a memory.

In order to achieve the above object, the present invention provides an ultrasound diagnostic apparatus configured to inspect an inspection object using an ultrasonic beam, the apparatus comprising:

a probe having a plurality of elements arranged therein, the probe being configured to transmit the ultrasonic beam and receive an ultrasonic echo reflected by the inspection object, and to output an analog element signal according to the received ultrasonic echo;

a transmitter configured to cause the probe to transmit the ultrasonic beam a plurality of times using at least two of the plurality of elements as transmission elements so as to form a predetermined transmission focus point;

a receiver configured to receive analog element signals output by at least two of the plurality of elements that, as reception elements, have received an ultrasonic echo corresponding to individual transmission of the ultrasonic beam and to perform a predetermined process;

an analog-to-digital converter configured to analog-to-digital convert the analog element signals processed by the receiver into first element data formed by a digital element signal;

a data processor configured to generate second element data corresponding to any one of a plurality of first element data from the plurality of first element data; and a frequency information acquiring unit configured to acquire information on a transmission frequency of the ultrasonic beam transmitted from the probe;

wherein the data processor generates the second element data using the plurality of first element data on the basis of the information on a transmission frequency acquired by the frequency information acquiring unit.

In the ultrasound diagnostic apparatus, the data processor preferably generates the second element data by superimposing the plurality of first element data according to reception times at which the elements have received the ultrasonic echo and positions of the elements.

In addition, preferably, the ultrasound diagnostic apparatus further comprises an element data selector configured to select the plurality of first element data used for generating the second element data in the data processor on the basis of the information on a transmission frequency acquired by the frequency information acquiring unit;

wherein the data processor generates the second element data using the plurality of first element data selected by the element data selector.

Further, the element data selector preferably selects at least one of the first element data where a time difference in reception time between the first element data when the data processor performs the superimposition is in a range of ¼ to ¾ of a cycle of the transmission frequency.

In addition, the element data selector preferably selects the first element data where a time difference in reception time between element data of interest is closest to a ½ cycle of the transmission frequency.

Further, the transmitter preferably changes at least one of a center element and a transmission direction of the ultrasonic beam and causes the probe to transmit the ultrasonic beam a plurality of times.

In addition, the data processor preferably generates the second element data using at least one of the plurality of first element data obtained by transmission of the ultrasonic beam where the center elements are different to each other and the plurality of first element data obtained by transmission of the ultrasonic beam where the transmission directions are different to each other.

Further, the data processor preferably generates the second element data from the plurality of first element data obtained by transmission of the ultrasonic beam where transmission regions overlap.

Preferably, the ultrasound diagnostic apparatus further comprises a phasing addition section which performs phasing addition on the first element data and generates first reception data;

wherein the phasing addition section performs phasing addition on each of the plurality of first element data with a line corresponding to the same element set as the center, and generates a plurality of first reception data; and wherein the data processor generates second reception data corresponding to any one of the plurality of first reception data from the plurality of a first element data.

In addition, the present invention provides a signal processing method for an ultrasound diagnostic apparatus for inspecting an inspection object using a probe having a plurality of elements arranged therein, the probe transmitting an ultrasonic beam, receiving an ultrasonic echo reflected by the inspection object, and outputting an analog element signal according to the received ultrasonic echo, the method comprising:

in the probe, a step of transmitting an ultrasonic beam a plurality of times so as to form a predetermined transmission focus point using at least two of the plurality of elements as transmission elements;

a step of receiving an ultrasonic echo corresponding to individual transmission of the ultrasonic beam with at least two of the plurality of elements as reception elements and outputting an analog element signal;

a step of analog-to-digital converting the analog element signal into first element data formed by a digital element signal;

a step of performing data processing for generating second element data corresponding to any one of the plurality of first element data from the plurality of first element data; and a step of acquiring information on a transmission frequency of the ultrasonic beam transmitted from the probe;

wherein, in the step of performing data processing, the second element data is generated using the plurality of first element data on the basis of the information on a transmission frequency acquired by the step of acquiring information on a transmission frequency.

Further, a non-transitory computer-readable recording medium having stored therein a program that causes a computer to execute a signal processing method for an ultrasound diagnostic apparatus for inspecting an inspection object using a probe having a plurality of elements arranged therein, the probe transmitting an ultrasonic beam, receiving an ultrasonic echo reflected by the inspection object, and outputting an analog element signal according to the received ultrasonic echo, the method comprising:

in the probe, a step of transmitting an ultrasonic beam a plurality of times so as to form a predetermined transmission focus point using at least two of the plurality of elements as transmission elements;

a step of receiving an ultrasonic echo corresponding to individual transmission of the ultrasonic beam with at least two of the plurality of elements as reception elements and outputting an analog element signal;

a step of analog-to-digital converting the analog element signal into first element data formed by a digital element signal;

a step of performing data processing for generating second element data corresponding to any one of the plurality of first element data from the plurality of first element data; and a step of acquiring information on a transmission frequency of the ultrasonic beam transmitted from the probe;

wherein, in the step of performing data processing, the second element data is generated using the plurality of first element data on the basis of the information on a transmission frequency acquired in the step of acquiring information on a transmission frequency.

According to the present invention, because data superimposing is performed according to the transmission frequency when correcting the data by superimposing a plurality of data obtained by different instances of transmission, ghost signals can be eliminated by performing superimposition a small number of times, a high quality ultrasound image can be obtained while preventing a decrease in the frame rate, and increases in costs can be prevented since it is not necessary to increase the capacity of a memory.

BRIEF DESCRIPTION OF THE DRAWINGS

FIGS. 4A and 4C are each conceptual diagrams for illustrating transmission and reception of ultrasonic waves according to an ideal ultrasonic beam, and FIGS. 4B and 4D are each conceptual diagrams illustrating element data obtained by the transmission and reception of ultrasonic waves.

FIGS. 5A and 5C are each conceptual diagrams for illustrating the transmission and reception of ultrasonic waves according to an actual ultrasonic beam, and FIGS. 5B and 5D are each conceptual diagrams illustrating element data obtained by the transmission and reception of ultrasonic waves.

FIGS. 7A, 7B, and 7C are conceptual diagrams for illustrating element data for a true signal and the delay time and a state in which the element data are superimposed. FIGS. 7D, 7E, and 7F are conceptual diagrams for illustrating element data for a ghost signal and the delay time and a state in which the element data are superimposed. FIG. 7G is a conceptual diagram for illustrating a state in which element data corresponding to a plurality of elements are superimposed, and FIG. 7H is a conceptual diagram for illustrating the result of superimposing the element data in FIG. 7G.

FIGS. 10A to 10D are diagrams for illustrating methods for selecting element data.

FIGS. 17A to 17C are diagrams for illustrating phasing addition and superimposition processing in the data processor illustrated in FIG. 13.

DETAILED DESCRIPTION OF THE INVENTION

Below, detailed description will be given of the ultrasound diagnostic apparatus, the signal processing method, and the program of the present invention on the basis of a favorable first embodiment illustrated in the accompanying drawings.

Figure 1:
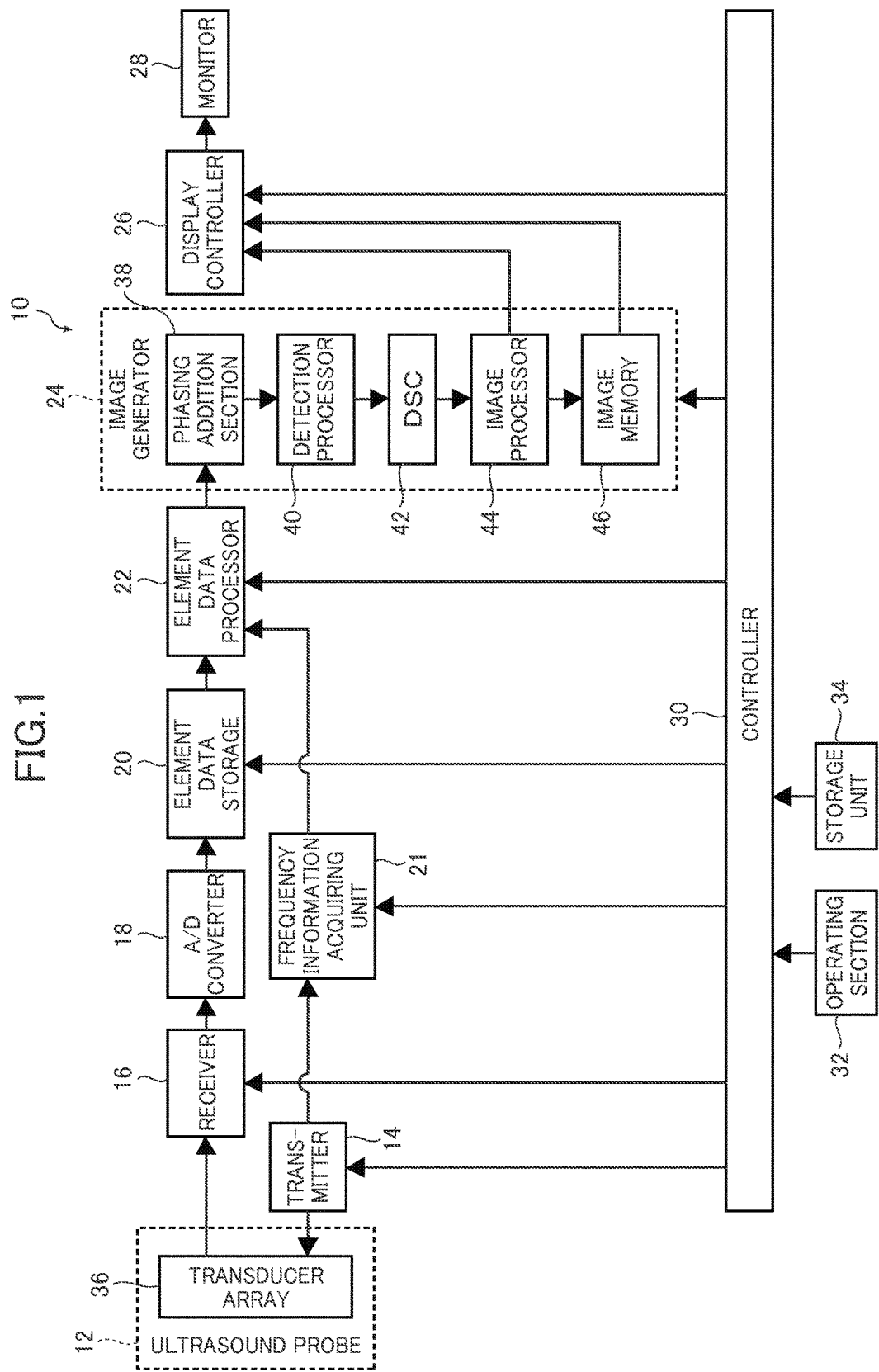
FIG. 1 is a block diagram conceptually illustrating an example of a configuration of an ultrasound diagnostic apparatus of the present invention.

FIG. 1 is a block diagram conceptually illustrating an example of the ultrasound diagnostic apparatus of the present invention which implements the signal processing method of the present invention.

As illustrated in FIG. 1, an ultrasound diagnostic apparatus 10 includes an ultrasound probe 12, a transmitter 14 and a receiver 16 connected with the ultrasound probe 12, an analog-to-digital (A/D) converter 18, an element data storage 20, a frequency information acquiring unit 21, an element data processor 22, an image generator 24, a display controller 26, a monitor 28, a controller 30, an operating section 32, and a storage unit 34.

In the illustrated example, the transmitter 14, the receiver 16, the A/D converter 18, the element data storage 20, the frequency information acquiring unit 21, the element data processor 22, the image generator 24, the display controller 26, the monitor 28, the controller 30, the operating section 32, and the storage unit 34 form the apparatus main body of the ultrasound diagnostic apparatus 10.

The ultrasound probe 12 is a known ultrasound probe used in a normal ultrasound diagnostic apparatus.

The ultrasound probe 12 (hereinafter, referred to as the probe 12) has a transducer array 36 in which ultrasound transducers are one-dimensionally or two-dimensionally arranged.

When taking an ultrasound image of an inspection object (hereinafter, referred to as a subject), the ultrasound transducers each transmit ultrasonic beams to the subject in accordance with a driving signal supplied from the transmitter 14, receive ultrasonic echoes reflected by the subject, and output a reception signal according to the strength of the received ultrasonic waves.

Each ultrasound transducer is configured by an oscillator where electrodes are formed at both ends of a piezoelectric body formed of, for example, a piezoelectric ceramic represented by lead zirconate titanate (PZT), a piezoelectric polymer represented by polyvinylidene fluoride (PVDF), a piezoelectric monocrystal represented by lead magnesium niobate-lead titanate solid solution (PMN-PT), or the like.

When a pulsed or continuous wave voltage is applied to the electrodes of the oscillator, the piezoelectric body expands and contracts according to the applied voltage, and pulsed or continuous ultrasonic waves are generated from each oscillator. In addition, the ultrasonic waves generated from the respective oscillators converge to a set focus point and are combined (that is, transmission focusing is performed on the ultrasonic waves) according to a driving delay of each of the oscillators, thereby forming an ultrasonic beam.

In addition, the oscillators expand and contract due to ultrasonic echoes reflected inside the subject being incident thereto and electric signals are generated according to the size of the expansion and contraction. The electric signals are output to the receiver 16 as the reception signals (analog element signals).

The transmitter 14 has, for example, a plurality of pulse generators and supplies a driving signal (applies a driving voltage) to each of the ultrasound transducers (oscillators) of the probe 12.

The transmitter 14 performs transmission focusing for adjusting the delay amount of the driving signal (application timing of the driving voltage) and supplies the driving signal to the ultrasound transducers on the basis of a transmission delay pattern selected by the controller 30 so as to form an ultrasonic beam where the ultrasonic waves transmitted by a predetermined number (a plurality) of ultrasound transducers converges to a set focus point.

Accordingly, a desired ultrasonic beam is transmitted from the probe 12 (the transducer array 36) to the subject.

In response to a control signal from the controller 30, the receiver 16 receives reception signals output by a predetermined number (a plurality) of ultrasound transducers corresponding to a single ultrasonic beam transmission, performs predetermined processing such as amplification, and supplies the result to the A/D converter 18.

Here, the method of transmitting and receiving the ultrasonic waves in the ultrasound diagnostic apparatus 10 of the present invention is basically the same as for a known ultrasound diagnostic apparatus.

Accordingly, in a single transmission and reception of ultrasonic waves, which is the transmission of one ultrasonic beam and the reception of ultrasound echo corresponding to this transmission, neither the number of ultrasound transducers (the number of transmission openings) which generate the ultrasonic waves nor the number of ultrasound transducers (the number of reception openings) which receive the ultrasonic waves, i.e., the receiver 16 which receives the reception signal, is limited as long as there is more than one of each. In addition, in a single transmission and reception, the number of openings may be the same or different in the transmission and the reception.

In addition, with ultrasonic beams adjacent in at least the azimuth direction (the arrangement direction of the ultrasound transducers), when transmission regions overlap, neither the number of times (number of sound rays) of the transmission and reception of the ultrasonic waves for forming one ultrasound image nor the intervals of the ultrasound transducers (center elements), that is, the density of the scanning lines/sound rays, in the center of the transmission and reception is limited. Accordingly, the transmission and reception of the ultrasonic waves may be performed with all of the ultrasound transducers corresponding to the region scanned with ultrasonic waves as the center elements, or the transmission and reception of the ultrasonic waves may be performed with ultrasound transducers at predetermined intervals, such as every two transducers or every four transducers, as the center elements.

In addition, in order to form one ultrasound image, transmission and reception is performed at a plurality of positions (lines) by sequentially moving the transmission and reception positions in the same manner as known ultrasound diagnostic apparatuses.

The A/D converter 18 A/D converts the analog reception signal supplied from the receiver 16 into element data (first element data) which is a digital reception signal.

The A/D converter 18 supplies the A/D converted element data to the element data storage 20.

The element data storage 20 sequentially stores the element data supplied from the A/D converter 18. In addition, the element data storage 20 stores information (for example, the depth of the reflecting position of the ultrasonic waves, the density of the scanning lines, or a parameter indicating a visual field width) relating to the frame rate input from the controller 30 in association with each of the element data.

Preferably, the element data storage 20 stores all of the element data corresponding to at least one ultrasound image (an ultrasound image of one frame) and does not delete the element data of the ultrasound image before display or during display at least until the display of the ultrasound image is finished.

The frequency information acquiring unit 21 acquires information on the transmission frequency of the ultrasonic beam, which is transmitted from the ultrasound probe 12, from the transmitter 14 or from the controller 30.

The frequency information acquiring unit 21 supplies the acquired transmission frequency information to an element data selector 47 of the element data processor 22.

The element data processor 22 generates processed element data (second element data) corresponding to each of the element data by superimposing the element data.

Specifically, under the control of the controller 30, the element data processor 22 superimposes the element data out of the element data stored in the element data storage 20 and obtained by a predetermined number (a plurality) of ultrasonic beam transmissions for which the ultrasound transducers in the center, i.e., the elements in the center (center elements), are different and the transmission regions of the ultrasonic beams overlap, according to the time at which each of the ultrasound transducers receives the ultrasonic echoes and the positions of the ultrasound transducers, thereby generating processed element data corresponding to the element data (element data of an element of interest to be described below).

Here, the element data processor 22 generates processed element data on the basis of the transmission frequency information supplied from the frequency information acquiring unit 21.

The processing in the element data processor 22 will be described in detail below.

The element data processor 22 sends the generated processed element data to the image generator 24.

The image generator 24 generates reception data (sound ray signal) from the processed element data supplied from the element data processor 22 under the control of the controller 30 and generates an ultrasound image from this reception data.

The image generator 24 includes the phasing addition section 38, the detection processor 40, the digital scan converter (DSC) 42, the image processor 44, and the image memory 46.

The phasing addition section 38 performs a reception focusing process by performing matching addition on the processed element data generated by the element data processor 22, and generates reception data.

As described above, in the transducer array 36 of the probe 12, a plurality of elements (ultrasound transducers) is one-dimensionally or two-dimensionally arranged. Accordingly, the distance to one reflection point in the subject is different for each ultrasound transducer. Therefore, even with ultrasonic echoes reflected at the same reflection point, the time for the ultrasonic echoes to arrive at each of the ultrasound transducers is different. The phasing addition section 38 performs a digital reception focusing process and generates reception data by performing matching addition on the processed element data to which a delay time is applied by delaying each signal of the processed element data by an amount equivalent to the difference in the arrival time (delay time) of ultrasonic echoes for each of the ultrasound transducers, according to a reception delay pattern selected by the controller 30.

The phasing addition section 38 supplies the generated reception data to the detection processor 40.

Figure 2:
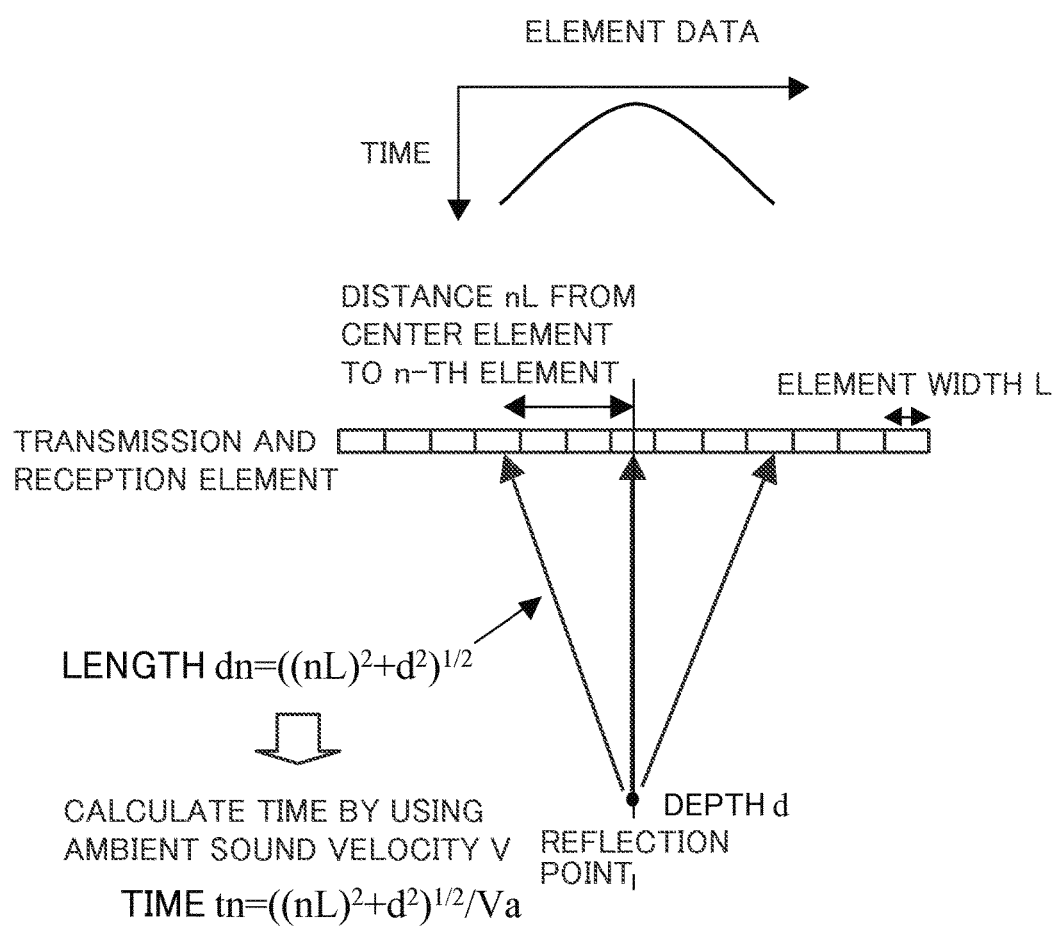
FIG. 2 is a conceptual diagram for describing an example of a reception focusing process in the ultrasound diagnostic apparatus depicted in FIG. 1.

FIG. 2 illustrates an example of the reception focusing process.

Here, FIG. 2 illustrates a case of a linear probe where the plurality of ultrasound transducers of the probe 12 is arranged in a row in the left and right direction in the diagram. However, the concept may be similarly applied even in the case of a convex probe where only the probe shape is different.

When the width of each of the ultrasound transducers in the azimuth direction is taken to be L, the distance up to the n-th ultrasound transducer from the ultrasound transducer in the center of the azimuth direction toward the end section is nL.

As illustrated in the same diagram, when the reflection point of the ultrasonic waves is taken to be at a position at a distance (depth) d, which is perpendicular to the arrangement direction, from the center ultrasound transducer, the distance (length) $d_n$ between the n-th ultrasound transducer and the reflection point is calculated using the formula (1).

$$d_n = ((nL)^2 + d^2)^{1/2} \qquad (1)$$

Accordingly, using the ultrasound sound velocity (ambient sound velocity) Va in the subject, the time $t_n$ for the ultrasonic echoes to reach (be received by) the n-th ultrasound transducer from the reflection point is calculated using Formula (2).

$$t_n = d_n/Va = ((nL)^2 + d^2)^{1/2}/Va \qquad (2)$$

As described above, the distance between the ultrasound transducers and the reflection point is different for each ultrasound transducer. Therefore, in the case of this example, as shown in the graph at the top of the same diagram, the arrival time $t_n$ of the ultrasonic echoes is longer for the ultrasound transducers toward the end section sides in the arrangement direction.

Specifically, when the time until the ultrasonic waves are received by the center ultrasound transducer from the reflection point is taken to be $t_1$, the ultrasonic waves received by the n-th ultrasound transducer are delayed by the time $\Delta t = t_n - t_1$ with respect to the ultrasonic waves received by the center ultrasound transducer. In the present example, the delay time $\Delta t$ is a reception delay pattern.

The phasing addition section 38 performs phasing addition using a delay time represented by the time $\Delta t$ described above, performs the reception focusing process, and generates reception data for signals corresponding to each of the ultrasound transducers.

After performing correction of the attenuation due to the distance according to the depth of the reflection position of the ultrasonic waves on the reception data generated by the phasing addition section 38, the detection processor 40 generates B mode image data formed by tomographic image information (brightness image information) in the subject by performing envelope detection processing.

The digital scan converter (DSC) 42 converts (raster converts) the B mode image data generated by the detection processor 40 into image data corresponding to a normal television signal scanning system.

The image processor 44 performs various necessary image processing such as gradation processing on the B mode image data input from the DSC 42 to create B mode image data for display. The image processor 44 outputs the image processed B mode image data to the display controller 26 for display and/or stores the image processed B mode image data in the image memory 46.

The image memory 46 is a known storage (a storage medium) which stores the B mode image data processed by the image processor 44. The B mode image data stored in the image memory 46 is read out by the display controller 26 for display on the monitor 28 as necessary.

The display controller 26 uses the B mode image data on which the predetermined image processing is performed by the image processor 44 to display an ultrasound image on the monitor 28.

The monitor 28 includes a display device such as an LCD, and displays an ultrasound image under the control of the display controller 26.

The controller 30 controls each section of the ultrasound diagnostic apparatus 10 on the basis of instructions input from the operating section 32 by an operator.

In addition, the controller 30 supplies various types of information input by the operator using the operating section 32 to necessary units. For example, in a case where information necessary for calculating the delay time used in the element data processor 22 and the phasing addition section 38 of the image generator 24 and information necessary for element data processing in the element data processor 22 are input by the operating section 32, the information is supplied to each section such as the transmitter 14, the receiving section 16, the element data storage 20, the frequency information acquiring unit 21, the element data processor 22, the image generator 24, and the display controller 26 as necessary.

The operating section 32 is a section for the operator to make input operations, and can be constituted by a keyboard, a mouse, a trackball, a touch panel, or the like.

In addition, the operating section 32 is provided with an input function for the operator to input various types of information as necessary. For example, the operating section 32 is provided with an input function for inputting information of the probe 12 (the ultrasound transducer); information relating to the generation of the processed element data such as the transmission opening and the reception opening in the probe 12 (the transducer array 36), the number of element data to be superimposed, or the generation method; the focus point position of the ultrasonic beam; and the like.

The above are input, for example, by selecting the photograph site (the examination site), selecting the image quality, selecting the depth of the ultrasound image to be photographed, or the like.

The storage unit 34 stores information necessary for the controller 30 to operate and control the ultrasound diagnostic apparatus such as information relating to an operation program for the controller 30 to execute control of each section of the ultrasound diagnostic apparatus 10, the transmission delay pattern and the reception delay pattern, and the generation of processed element data; information on the probe 12 input from the operating section 32; information on the transmission opening, the reception opening, and the focus point position.

In the storage unit 34, it is possible to use a known recording medium such as a hard disk, a flexible disk, an MO, an MT, a RAM, a CD-ROM, or a DVD-ROM.

Here, the element data processor 22, the phasing addition section 38, the detection processor 40, the DSC 42, the image processor 44, the display controller 26, and the like in the ultrasound diagnostic apparatus 10 are configured by a CPU and an operation program for causing the CPU to perform various types of processing. However, in the present invention, these units may be configured by a digital circuit.

As described above, the element data processor 22 generates processed element data by superimposing element data out of the element data (the unprocessed element data) stored in the element data storage 20 and obtained by a predetermined number (a plurality) of ultrasonic beam transmissions, for which the center ultrasound transducers (the center elements) are different and the transmission regions of the ultrasonic beams overlap, according to the time of being received by each ultrasound transducer and the position of the ultrasound transducers.

Here, in the following description, the ultrasound transducers are also referred to simply as "elements".

Figure 3:
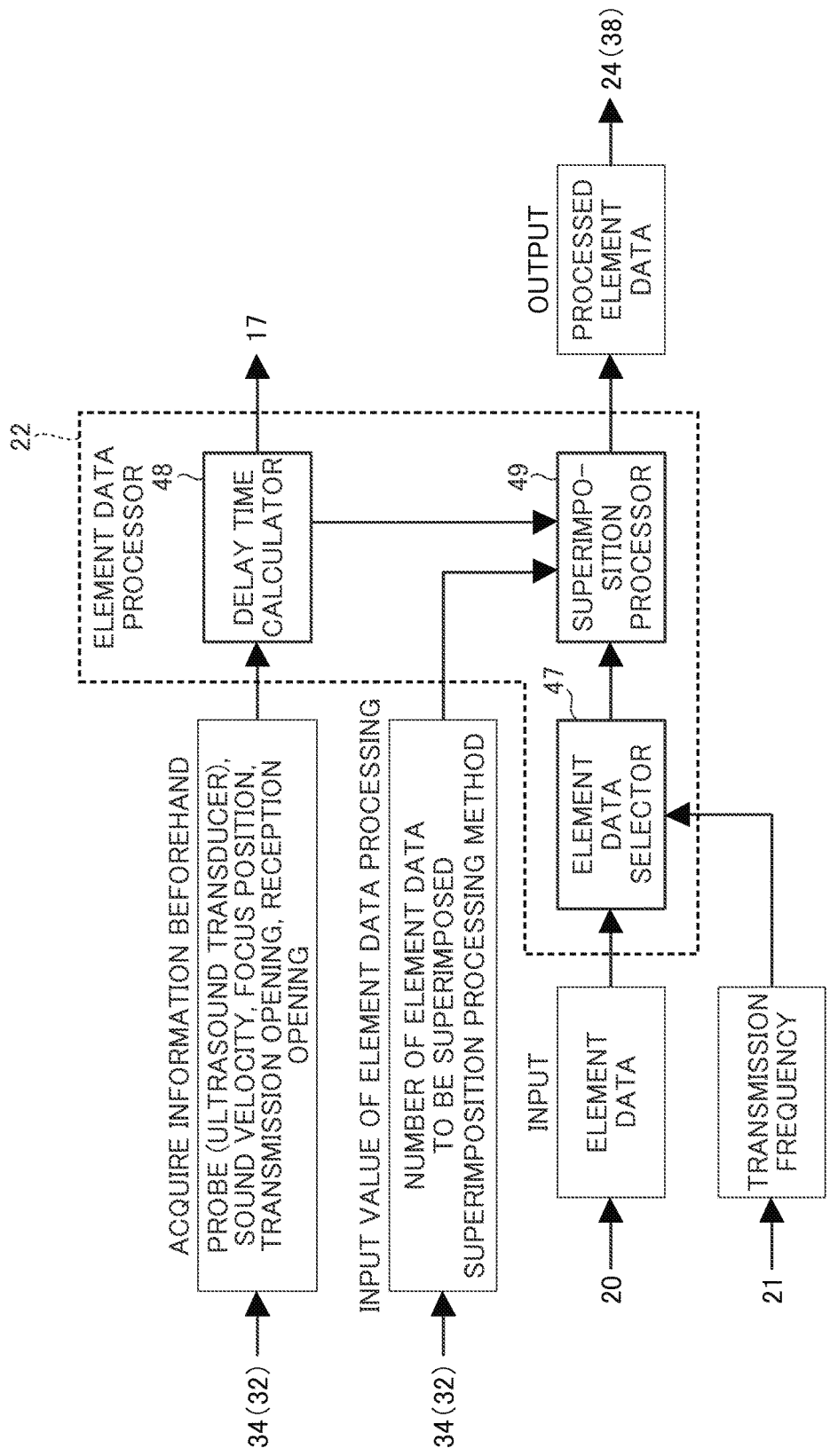
FIG. 3 is a block diagram conceptually illustrating an example of a configuration of an element data processor of the ultrasound diagnostic apparatus depicted in FIG. 1.

FIG. 3 is a block diagram conceptually illustrating the configuration of the element data processor 22.

As illustrated in FIG. 3, the element data processor 22 includes the element data selector 47, a delay time calculator 48, and a superimposition processor 49.

The delay time calculator 48 acquires in advance information, which is input from the operating section 32 or input from the operating section 32 and stored in the storage unit 34, on the probe 12 (ultrasound transducer (element)), the focus point position of the ultrasonic beam, the sampling point position (output position of the element data), the transmission openings and reception openings of the probe 12, and the like. In addition, the delay time calculator 48 calculates the delay time of the ultrasonic echoes received by the elements of the reception openings, that is, the element data, on the basis of the geometric positions of the elements of the transmission openings which oscillate the ultrasonic waves in order to transmit (generate) the ultrasonic beams and the elements of the reception openings which receive the ultrasonic echoes from the subject.

The delay time calculator 48 supplies the information on the calculated delay time to the superimposition processor 49.

The element data selector 47 selects element data used in the superimposing in the superimposition processor 49 (element data for which the center elements are different and which is obtained by ultrasonic beams for which transmission regions overlap (two or more of element data generated for each of two or more target regions)) and reads out the selected element data from the element data storage 20 on the basis of information, which is input from the operating section 32 or input from the operating section 32 and stored in the storage unit 34, relating to the element data processing such as the number of element data to be superimposed, the superimposition processing method, and the like, and information on the transmission frequency supplied from the frequency information acquiring unit 21.

The element data selector 47 supplies the read element data to the superimposition processor 49.

The element data selector 47 will be described in detail below.

On the basis of the delay time corresponding to each of the element data calculated by the delay time calculator 48 by acquiring the element data read out from the element data selector 47, the superimposition processor 49 generates processed element data by matching two or more of element data according to the reception time, that is, matching the time, and by matching and superimposing the absolute positions of the elements of the receiving search probes.

Below, detailed description will be given of the processing of the element data performed by the element data processor 22.

Firstly, description will be given of a relationship between ultrasonic beams from the transmission elements and element data obtained by the reception elements in a case where, in the ultrasound probe 12, the ultrasonic beams are transmitted to the subject from the transmission opening, that is, the element (hereinafter, simply referred to as the transmission element) which sends out the ultrasonic waves in order to transmit the ultrasonic beams, and the element data is obtained by receiving the ultrasonic echoes generated by interaction with the subject in the reception opening, that is, in the element (hereinafter, simply referred to as the reception element) which receives the ultrasonic echoes.

As an example, as illustrated in FIG. 4A, the ultrasonic beams are transmitted with three elements 52c to 52e as transmission elements and the ultrasonic echoes are received with seven elements 52a to 52g as reception elements. Next, as illustrated in FIG. 4C, the ultrasonic beams are transmitted with three elements 52d to 52f as transmission elements by moving (hereinafter, also referred to as shifting) the elements by one element in the azimuth direction and each of the element data is acquired by receiving the ultrasonic echoes with seven elements 52b to 52h as the reception elements.

That is, the center element (the element in the center) is the element 52d in the example illustrated in FIG. 4A and the center element is the element 52e in the example illustrated in FIG. 4C.

Now, an ideal case will be considered in which ultrasonic beams 56 transmitted to the inspection object region including a reflection point 54 are converged to a focus point 58 and narrowed to the element spacing or less.

As illustrated in FIG. 4A, when ultrasonic beams 56 are transmitted from the elements 52c to 52e which are transmission elements with the element 52d directly above (on a straight line linking the reflection point and the focus point) the reflection point 54 as the center element and the element data is acquired by receiving the ultrasonic echoes in the elements 52a to 52g which are the reception elements, the focus point 58 of the ultrasonic beam 56 is on a straight line linking the element 52d which is the center element and the reflection point 54. In such a case, because the ultrasonic beam 56 is transmitted up to the reflection point 54, the ultrasonic echoes reflected from the reflection point 54 are generated.

The ultrasonic echoes from the reflection point 54 are received by the elements 52a to 52g which are the reception elements after passing through a reception path 60 extending at a predetermined angle and element data 62 as illustrated in FIG. 4B is obtained by the elements 52a to 52g. Here, in FIG. 4B, the vertical axis represents the time and the horizontal axis represents the position (the position of the elements) in the azimuth direction corresponding to FIG. 4A (the same applies to FIG. 4D).

In contrast, as illustrated in FIG. 4C, in a case where the center element is shifted by one element, the element 52e next to the element 52d directly above the reflection point 54 becomes the center element.

The ultrasonic beam 56 is transmitted from the elements 52d to 52f which are transmission elements with the element 52e as the center element and the ultrasonic echoes are received in the elements 52b to 52h which are the reception elements. At this time, in the same manner, when the ultrasonic beam 56 is ideal, the reflection point 54 is not present in the transmission direction of the ultrasonic beam 56, that is, on a straight line linking the center element 52e and the focus point 58. Accordingly, the ultrasonic beam 56 is not transmitted to the reflection point 54.

Therefore, because ultrasonic echoes reflected by the reflection point 54 are not generated and the elements 52b to 52h, which are reception elements, do not receive ultrasonic echoes from the reflection point 54, the element data does not include a reflected signal from the reflection point as illustrated in FIG. 4D (the signal strength of the element data is 0).

However, because the actual ultrasonic beam is diffused after converging to the focus point 58 as in the ultrasonic beam 64 illustrated in FIG. 5A and FIG. 5C, the actual ultrasonic beam has a width wider than the element spacing.

Here, similarly to FIG. 4A, in a case where the ultrasonic beam 64 is transmitted with the elements 52c to 52e as the transmission elements and the element 52d directly above the reflection point 54 as the center element as in FIG. 5A, even when the ultrasonic beam 64 is wide, the focus point 58 is on a straight line linking the element 52d and the reflection point 54. Accordingly, the ultrasonic beam 64 is reflected at the reflection point 54 and ultrasonic echoes are generated.

As a result, in the same manner as the case of FIG. 4A, the ultrasonic echoes from the reflection point 54 are received by the elements 52a to 52g which are the reception elements after passing through the reception path 60 which widens at a predetermined angle, and, similarly, true element data 66 as illustrated in FIG. 5B is obtained.

Next, similarly to FIG. 4C, as illustrated in FIG. 5C, the ultrasonic beam 56 is transmitted after shifting the center element by one element, setting the adjacent element 52e as the center element, and setting the elements 52d to 52f as the transmission elements, and the ultrasonic echoes are received with the elements 52b to 52h as the reception elements. Even in such a case, because the ultrasonic beam 64 is wide, the ultrasonic beam 64 is transmitted to (arrives at) the reflection point 54 even when the reflection point 54 is not present in the transmission direction of the ultrasonic waves, that is, on a straight line linking the element 52e which is the center element and the focus point 58.

Therefore, ultrasonic echoes which are not inherently present or so-called ghost reflected echoes are generated in the transmission direction of the ultrasonic beam from the reflection point 54. The ghost reflected echoes from the reflection point 54 are received by the elements 52b to 52h which are reception elements after passing through the reception path 60 which widens at a predetermined angle as illustrated in FIG. 5C. As a result, ghost element data 68 as illustrated in FIG. 5D is obtained by the elements 52b to 52h.

In this manner, the ghost element data 68 is a cause of the precision of the ultrasound image generated from the element data decreasing.

The element data processor 22 calculates the delay time corresponding to the element data in the delay time calculator 48, and generates processed element data constituted by high precision element data for which the ghost signals are attenuated by the true element data being emphasized by the superimposition processor 49 superimposing two or more of element data according to the delay time and the absolute position of the elements.

As described above, the delay time calculator 48 calculates the delay time of the element data received by each of the reception elements (reception openings).

That is, the propagation distance of the ultrasonic beam 64 illustrated in FIG. 5C is the sum of the transmission path where the ultrasonic beam 64 reaches the reflection point 54 from the element 52e which is the center element via the focus point 58 and the reception path where the ghost reflected echoes from the reflection point 54 reach each of the elements 52b to 52h which are the reception elements.

The propagation distance of the ultrasonic beam 64 illustrated in FIG. 5C is longer than the propagation distance of the ultrasonic beam 64 illustrated in FIG. 5A, that is, the sum of the transmission path where the ultrasonic beam 64 reaches the reflection point 54 from the center element 52d via the focus point 58 and the reception path where the true ultrasonic echoes from the reflection point 54 reach the elements 52a to 52g which are the reception elements.

Therefore, the ghost element data 68 as illustrated in FIG. 5D is delayed with respect to the true element data 66 as illustrated in FIG. 5B.

In the delay time calculator 48 of the element data processor 22, the time difference between the true element data and the ghost element data, that is, the delay time is calculated from the sound velocity, the transmission elements, the focus point of the ultrasonic beam, the reflection point of the subject, and the geometric arrangement of the reception elements.

Accordingly, in the calculation of the delay time, information such as the shape of the probe 12 (the element spacing, the probe being linear, convex, or the like), the sound velocity, the position of the focus point, the transmission opening, and the reception opening is necessary. In the delay time calculator 48, the information input by the operating section 32 or stored in the storage unit 34 is acquired to calculate the delay time. Here, a fixed value (for example, 1540 m/sec) may be used as the sound velocity. Alternatively, in a case where there is a sound velocity calculator, a sound velocity (ambient sound velocity) calculated by the sound velocity calculator may be used as the sound velocity, or an operator may input the sound velocity.

It is possible for the delay time to be calculated from the difference in the propagation time calculated according to the sound velocity and the total length (propagation distance) of the transmission path of the ultrasonic beam from the transmission element to the reflection point via the focus point and the reception path of true reflected ultrasonic echoes or the ghost reflected signal from the reflection point up to the reception elements, which is calculated from the geometric arrangement of, for example, the transmission elements, the focus point of the ultrasonic beam, the reflection point of the subject, and the reception elements.

Figure 6A:
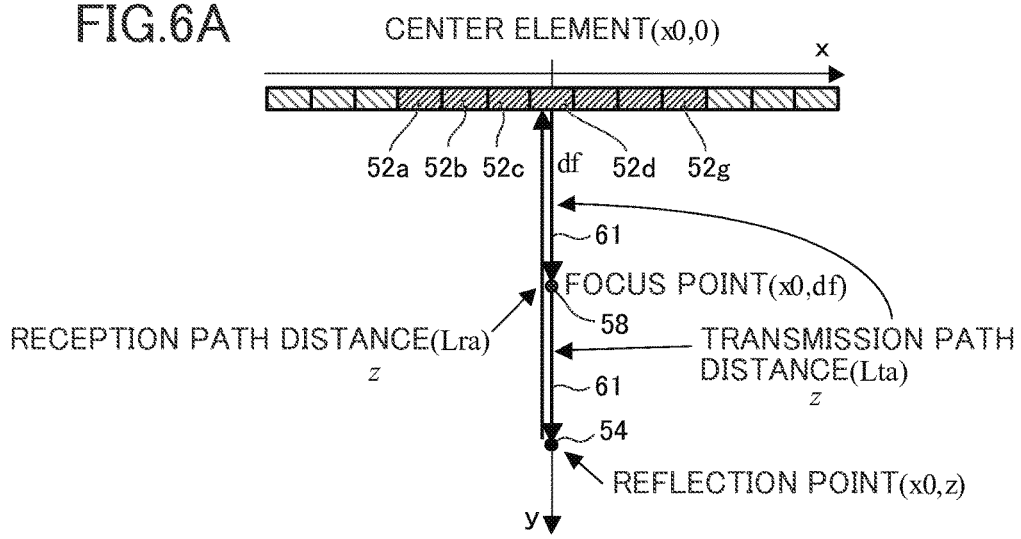
FIGS. 6A and 6B are conceptual diagrams for illustrating a path of sound waves in a case where the transmission and reception of ultrasonic waves are performed by center elements which are different to each other with respect to the same reflection point.
Figure 6B:
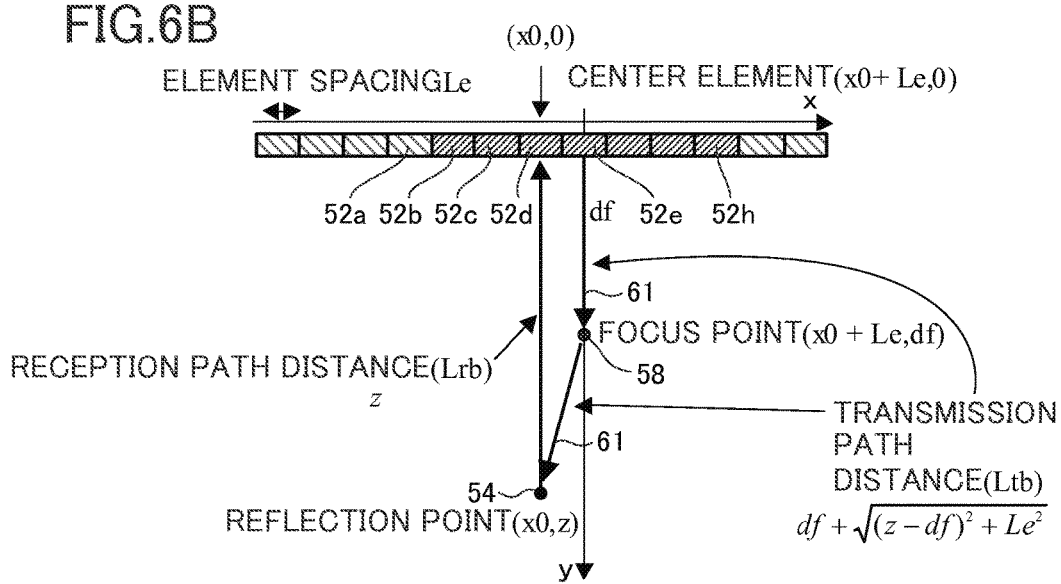

In the present invention, for example, as illustrated in FIG. 6A and FIG. 6B, it is possible to determine the length of the transmission path and the reception path of the ultrasonic beam in the case of the true ultrasonic echoes and the ghost reflected echoes. Here, in FIGS. 6A and 6B, the x direction is the azimuth direction and the y direction is the depth direction.

In addition, in FIG. 6A, the transmission and reception of the ultrasonic waves is performed in the same manner as in FIG. 5A and, in FIG. 6B, the transmission and reception of the ultrasonic waves is performed in the same manner as in FIG. 5C.

In the case of the true ultrasonic echoes, as illustrated in FIG. 6A (FIG. 5A), the element 52d which is the center element, the focus point 58, and the reflection point 54 are positioned on a straight line (the positions are matched in the azimuth direction). That is, the focus point 58 and the reflection point 54 are positioned directly below the center element 52d.

Accordingly, when the position of the element 52d which is the center element is taken to be coordinates (x0, 0) which are two dimensional x-y coordinates, the x coordinate of the focus point 58 and the reflection point 54 is also "x0". Below, the position of the focus point 58 in the transmission is taken to be coordinates (x0, df), the position of the reflection point 54 is taken to be coordinates (x0, z), and the element spacing is taken to be Le.

At this time, it is possible for the length (transmission path distance) Lta of a transmission path 61 of the ultrasonic beam from the element 52d which is the center element to the reflection point 54 via the focus point 58 and the length (the reception path distance) Lra of the reception path 60 of the true reflected ultrasonic echoes from the reflection point 54 to the element 52d to be calculated using Lta=Lra=z.

Accordingly, in the case of the true ultrasonic echoes, the propagation distance Lua of the ultrasonic echoes is Lua=Lta+Lra=2z.

Next, as illustrated in FIG. 6B, by shifting (shifting in the direction to the right in the diagram) the transmission element and the reception element by one element in the x direction (the azimuth direction), transmission and reception are performed with the element 52e as the center element. As illustrated in FIG. 5C, in this case, the echoes reflected at the reflection point 54 are the ghost reflected echoes.

The reflection point 54 is positioned directly below the element 52d (at the same position in the azimuth direction). Accordingly, as illustrated in FIG. 6B, in the transmission and the reception, the positions of the element 52e which is the center element and the reflection point 54 in the x direction are shifted in the x direction by one element, that is, by Le.

Because the coordinates of the element 52d whose position matches the reflection point 54 in the x direction are (x0, 0), the coordinates of the element 52e which is the center element become (x0+Le, 0) and the coordinates of the focus point 58 in the transmission become (x0+Le, df). Here, as described above, the coordinates of the reflection point 54 are (x0, z).

Accordingly, the length (transmission path distance) Ltb of the transmission path 61 of the ultrasonic beam arriving at the reflection point 54 from the element 52e, which is the center element, via the focus point 58 can be calculated using $Ltb=df+\sqrt{(z-df)^2+Le^2}$. On the other hand, the length (the reception path distance) Lrb of the reception path 60 of the ghost reflected signal from the reflection point 54 to the element 52*d* located directly below (at the same position in the x direction, i.e., the azimuth direction) can be calculated using $Lrb=z$.

Accordingly, the propagation distance Lub of the ultrasonic waves in the case of ghost reflected echoes is $Lub=Ltb+Lrb=df+\sqrt{(z-df)^2+Le^2}+z$.

In this manner, a value where the propagation distance Lua of the ultrasonic waves which is the total of the distance Lta of the transmission path 61 and the distance Lra of the reception path 60 determined by the geometric arrangement illustrated in FIG. 6A is divided by the sound velocity is the propagation time of the true ultrasonic echoes. In addition, a value where the propagation distance Lub of the ultrasonic waves which is the total of the distance Ltb of the transmission path 61 and the distance Lrb of the reception path 60 determined by the geometric arrangement illustrated in FIG. 6B is divided by the sound velocity is the propagation time of the ghost reflected echoes.

The delay time is determined from the difference between the propagation time of the true ultrasonic echoes when the x coordinates of the reflection point 54 and the center element are matched and the propagation time of the ghost reflected echoes when the x coordinates of the reflection point 54 and the center element are shifted by a single element spacing at a time.

Here, the geometric model of FIG. 6A and FIG. 6B is a model where the transmission path 61 goes via the focus point 58; however, the present invention is not limited thereto, and, for example, may be a path arriving directly at the reflection point 54 without going via the focus point 58.

In addition, the geometric model of FIG. 6A and FIG. 6B is for the case of a linear probe; however, without being limited thereto, it is possible to perform the geometric calculation in the same manner from the shape of the probe even with other probes.

For example, in the case of a convex probe, it is possible to perform the calculation in the same manner by setting the geometric model using the radius of the probe and angle of the element spacing.

In addition, in the case of a steer transmission, it is possible to calculate the delay time of the true element data and the ghost element data of the surroundings thereof from the positional relationship between the transmission elements and the reflection points using a geometric model taking information such as the transmission angle into consideration.

Furthermore, without being limited to a method of calculating the delay time according to a geometric model, by determining the delay time for every measuring condition from the measuring results of measuring the high brightness reflection point in accordance with the measuring conditions of the apparatus in advance and storing the delay times in the apparatus, the delay time for the same measuring conditions may be read out.

Figure 6C:
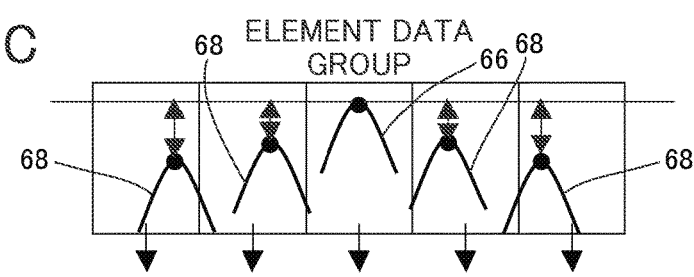
FIG. 6C is a conceptual diagram for illustrating element data obtained by a plurality of elements.

FIG. 6C illustrates the true element data 66 and the ghost element data 68.

In FIG. 6C, the center in the azimuth direction is the true element data 66, that is, element data (element data where the element 52*d* is taken to be the center element in the example in the diagram) obtained by transmission and reception where the positions of the center element and the reflection point 54 match in the x direction. In addition, both sides of the center are ghost element data, that is, element data (element data where the element 52*c* or the element 52*e* is taken to be the center element in the example in the diagram) obtained by transmission and reception where the positions of the center element and the reflection point 54 do not match in the x direction.

Figure 6D:
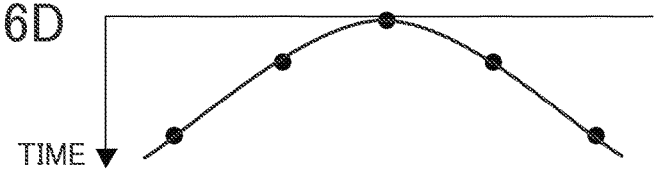
FIG. 6D is a conceptual diagram for illustrating the element data delay time illustrated in FIG. 6C.

In addition, FIG. 6D illustrates an example of the delay time of the ghost element data 68 with respect to the true element data 66 obtained by the geometric calculation described above. Centering on the true element data 66, the element data 68 of the ghost signal indicates that the time is symmetrically delayed in the x direction, that is, the azimuth direction.

Here, in this manner, it is also possible for the delay time calculated in the delay time calculator 48 of the element data processor 22 to be used in the delay correction in the phasing addition section 38.

As will be described in detail below, in the present invention, by superimposing element data, which is obtained by the transmission of the ultrasonic beam where at least a portion of the ultrasonic beam overlaps and for which the center element is different, on element data, which is obtained by the transmission (the transmission and reception of the element of interest) of an ultrasonic beam where a certain element of interest is the center element, by matching the reception time of the ultrasonic echoes and the position of the elements, the processed element data (second element data) of the element of interest is generated (the element data of the element of interest is rebuilt).

In FIG. 6A, the reflection point 54 indicates the position (the output position of the element data) of a certain sampling point positioned directly below the element of interest (at the same position in the azimuth direction or on a straight line linking the element of interest and the focus point). In the present invention, the transmission and reception path to the sampling point in the transmission and reception of the element of interest is regarded as the transmission and reception path of the true element data and the transmission and reception path to the same sampling point in the transmission and reception (the transmission and reception from the surrounding elements) of the ultrasonic waves where the center element is different is regarded as the ghost transmission and reception path. The superimposition is performed by calculating the delay time from the difference between both transmission paths and matching the time of the element data using the delay time. In other words, the delay time is calculated and the superimposition of the element data is performed assuming that element data obtained by the transmission and reception of the element of interest is the true element data and element data obtained by the transmission and reception where the center element is different is the ghost element data.

In the present invention, the superimposition of the element data is performed by calculating the delay time with the same concept corresponding to all of the sampling points (the output position of all the element data) and the processed element data of each of the elements is generated.

Here, in fact, even when the positions of the sampling points (reflection points) are shifted in the azimuth direction (the x direction), the length of the reception path (the reception path distance Lrb) does not change. Accordingly, in relation to each of the elements of interest, the calculation of the delay times of the element data according to transmission and reception for which the center elements are different may be performed for every sampling point in the depth direction (the y direction).

In addition, it is not necessary to know which element data is the true element data in the superimposition processing. That is, although described in detail with reference to FIGS. 7A to 7H below, in the superimposition processing, the element data of the element of interest is automatically emphasized and remains when the element data is the true element data and the element data is canceled when the element data is ghost element data. That is, in a case where the element data of the element of interest is the true element data, the signal is emphasized by matching the process according to the delay time and, in a case where the element data of the element of interest is the ghost element data, the signal is canceled without matching the process according to the delay time.

Next, in the superimposition processor 49 of the element data processor 22 of the present invention, the superimposition processing of the element data is performed using the delay time calculated in the delay time calculator 48 in this manner.

FIGS. 7A to 7H illustrate an example of superimposition processing performed by the superimposition processor 49. Here, the example illustrated in FIGS. 7A to 7H is of a case where the number of element data is five and the number of superimposed element data is three.

FIG. 7A illustrates five pieces of element data obtained by performing the transmission and reception of the ultrasonic waves five times are lined up side by side. In addition, FIG. 7A represents a state where ultrasonic echoes are received after the ultrasonic beams are transmitted for each element data. The horizontal axis of each element data represents a reception element and displays the center element in the center in the transmission and reception of the ultrasonic beam in each of the element data. The vertical axis represents the reception time. In this example, transmission and reception of the ultrasonic waves is performed five times by shifting the center element by one element at a time, for example, in the above-described elements 52b to 52f or the like.

FIG. 7A illustrates a state in which one reflection point is present only directly below the center element in the center element data. That is, out of the five element data, the true ultrasonic echoes are received in the element data in the middle from the reflection point in the transmission and reception of the ultrasonic waves. That is, the element data in the middle is the true element data.

Regarding the two element data on both sides other than the element data in the middle, the reflection point is not present directly below the center element in the transmission and reception of the ultrasonic waves. However, due to the ultrasonic beam hitting the reflection point which is present directly below the transmission element of the element data in the middle according to the spread of the transmitted ultrasonic beam, the generated reflected echo element data, that is, the ghost element data is reflected.

The further the ghost element data is separated from the true element data, the longer the propagation time of the ultrasonic waves up to the reflection point, thus the reception time for the ghost element data is longer than for the true element data. In addition, the position of the reception element where the ultrasonic echoes from the reflection point are first received is directly above the reflection point (an element whose position in the azimuth direction matches the reflection point).

Here, the horizontal axes of each of the element data in FIG. 7A set the center element during the transmission of the ultrasonic beam in the center. Accordingly, in the examples illustrated in FIG. 7A, because transmission is carried out by shifting the center element by one element for each of the element data, the absolute position of the elements in the azimuth direction in each element data is shifted by one element at a time. In other words, in the element data in the middle, the reception element which first receives the reflected signal from the reflection point is the center element; however, in both adjacent element data, the reception element is shifted by one element from the element data in the middle, the element data on the right side is shifted by one element to the left, and the element data on the left side is shifted one element to the right. Furthermore, the element data on both ends is shifted by two elements from the element data in the middle, the element data at the right end is shifted by two elements to the left, and the element data at the left end is shifted by two elements to the right. In this manner, not only is the reception time longer for the ghost signals than for the true signal, but shifting is also generated with respect to the direction of the reception elements.

FIG. 7B illustrates an example of the delay time of the reception time with respect to the element data in the middle of the five element data illustrated in FIG. 7A.

In the superimposition processor 49, in a case where the element data in the middle is set as the element data of the element of interest, the delay time correction is performed according to the number of element data to be superimposed (three element data in the example in the diagram) centering on the element data of the element of interest using the delay time illustrated in FIG. 7B. Also, by shifting each element data by one element in the azimuth direction at both sides in the example in the diagram according to the difference of the element position on the element of interest (difference with the position of the center element), that is, by matching the phases, unprocessed element data for three element data are superimposed and determined as one superimposition processed element data for the element of interest.

That is, in the present example, the processed element data of the element data of the element of interest is generated by superimposing the element data (hereinafter, also referred to as the element data of the adjacent element), obtained by transmission and reception of the ultrasonic waves where the element adjacent to the element of interest is the center element, on the element data (hereinafter, also referred to as element data of the element of interest), obtained by the transmission and reception of the ultrasonic waves where the element of interest is the center element.

The superimposition processed element data of the element of interest obtained in this manner is illustrated in FIG. 7C.

As described above, the element data of the element of interest illustrated in FIG. 7A is true element data in which the reflection point is present directly below the center element (that is, the element of interest). In addition, the element data obtained by the transmission and reception where an element adjacent to the element of interest is the center element is also ultrasonic echo data where the ultrasonic waves are incident on the reflection point and reflected.

Accordingly, when performing the phase matching by performing delay time correction and azimuth direction shifting on the element data of the elements adjacent at both sides of the element data of the element of interest, the element data of the adjacent element and the element data of the element of interest overlap at a high brightness position because the phases match as illustrated in FIG. 7C. Therefore, for example, when the element data are added, the element data value indicates a large value (high brightness value). For instance, the element data indicates an emphasized value (high brightness value) even when an average value is determined by averaging.

In contrast, FIG. 7D illustrates an example of a case with the same element data as FIG. 7A; however, the center element of the element data adjacent to the left of the element data in the middle is the element of interest. That is, this example shows a case of the transmission and reception of ultrasonic waves where an element for which the reflection point is not present directly below is the center element, in which the center element is the element of interest. Accordingly, the element data where the element is the center element is ghost element data.

FIG. 7E is the same as FIG. 7B and illustrates an example of the delay time of the reception time with respect to the element data of the element of interest of the five element data illustrated in FIG. 7A. That is, because FIG. 7A and FIG. 7D are of the same element data, the delay time of the reception time with respect to the element data in the middle of the five element data illustrated in FIG. 7D is also the same.

In the superimposition processor 49, the delay time correction is performed according to the number of element data to be superimposed (three element data in the example in the diagram) centering on the element data of the element of interest using the delay time illustrated in FIG. 7E (that is, the same as FIG. 7B). Also, by shifting each element data by one element in the azimuth direction at both sides in the example in the diagram according to the difference of the element position on the element of interest (difference with the position of the center element), unprocessed element data for three element data are superimposed and determined as one superimposition processed element data for the element of interest.

The superimposition processed element data of the element of interest obtained in this manner is illustrated in FIG. 7F.

The element data of the element of interest illustrated in FIG. 7D is ghost element data. Therefore, even when phase matching is performed by performing delay time correction and azimuth direction shifting on the unprocessed element data of the adjacent element data on both sides of the element data of the element of interest, as illustrated in FIG. 7F, each element data of the adjacent element data and the element data of the element of interest do not overlap because the phases are not mutually matched. For this reason, because the phases do not match even when, for example, three element data are added, signals or the like where the phases are inverted cancel each other out, thus the added value is not large and, for example, a small value is indicated when the average value is determined by averaging.

In relation to the other element data, FIG. 7G illustrates a superimposed state of three adjacent element data for each of five element data in the example in the diagram as a result of performing the same delay time correction and azimuth direction shifting as for the element data of the element of interest. With respect to these, FIG. 7H illustrates the results after, for example, addition processing or averaging processing is carried out as the superimposition processing.

As illustrated in FIG. 7H, in a case where a center element where the reflection point is present directly below illustrated in FIG. 7A is the element of interest, the element data of the true signal is determined as superimposition processed element data having a high brightness value. In contrast, in all four element data of each of the two element data on both sides thereof, for the ghost element data, the element data where the phases do not match each other are added or averaged. Therefore, because the element data cancel each other out, the value of the ghost superimposition processed element data is lower than that of the superimposition processed element data having a high brightness value which is element data of a true signal, and it is possible to reduce the influence of the ghost element data on the true element data, or it is possible to reduce the influence thereof to a level which may be ignored.

That is, one or more of the element data which is obtained by transmission and reception of the ultrasonic waves for which the transmission regions of the ultrasonic beam overlap and for which the center elements are different are superimposed on element data (element data of the element of interest) where a certain element is set as the element of interest and which is obtained by transmission of an ultrasonic beam where this element of interest is the center element by performing time and azimuth direction position matching, and processed element data corresponding to the element data of the element of interest is generated. Accordingly (in other words, by performing rebuilding (correction) of the element data of the element of interest using element data according to transmission and reception where at least a portion of the ultrasonic beam overlap and the center element is different), the brightness level of the true element data is increased and it is possible to decrease the ghost element data.

Therefore, because it is possible to generate the ultrasound image with element data in such a case that the influence of the ghost is eliminated, that is, the focus points at all points on the sound ray are linked by performing phasing addition or detection processing on the processed element data, generating the reception data, and generating the ultrasound image, it is possible to generate an ultrasound image with high image quality, high brightness, and excellent sharpness.

Here, the generation of the processed element data is also referred to as multi-line processing in the following description.

In the present invention, the center element is the element in the center in the azimuth direction in a case where the number of openings of the transmission (the number of elements which perform the transmission of the ultrasonic waves) is an odd number.

On the other hand, in a case where the number of openings is an even number, any one of the elements in the center in the azimuth direction is set as the center element, or, assuming that there is an element in the middle of the azimuth direction, this element is set to be the center element. That is, in the case where the number of openings is an even number, a calculation may be performed with the assumption that there is a focus point on a line in the middle of the openings.

Here, as the superimposition processing method in the superimposition processor 49, an average value or a median value may be taken instead of only adding, or addition may be carried out after multiplication with a coefficient. Here, taking the average value or the median value may be considered equivalent to applying an averaging filter or a median filter at the element data level; however, an inverse filter or the like which performs normal image processing may also be applied instead of the averaging filter or the median filter.

Alternatively, when each of the element data to be superimposed is compared, the value is the maximum in a case where the element data are similar, the value is average in a case where the element data are not similar, and the value is intermediate in a case where the distribution is biased, but the superimposition processing may be changed on the basis of the feature amount of each of the element data to be superimposed without being limited thereto.

In addition, the number of element data to be superimposed on the element data of the element of interest is not limited to two in the example in the diagram and may be one or may be three or more. That is, the number of the element data to be superimposed on the element data of the element of interest may be appropriately set according to the required processing speed (the frame rate or the like), image quality, or the like.

Here, it is desirable that the number of element data to be superimposed on the element data of the element of interest match the extent of the spread of the beam width of the ultrasonic beam. Accordingly, in a case where the beam width changes according to the depth, the number of the element data to be superimposed may also be changed according to the depth.

In addition, because the beam width depends on the number of transmission openings, the number of element data to be superimposed may be changed according to the number of the transmission openings.

Here, in the multi-line processing above, the processed element data of the element data of the element of interest is generated by superimposing the element data where the center elements are different and which is obtained by a transmission of a plurality of ultrasonic beams for which the transmission direction of the ultrasonic beams is parallel (the angles are the same); however, the present invention is not limited thereto.

For example, the processed element data may be generated by superimposing the element data where the center elements are the same and which is obtained by the transmission of a plurality of ultrasonic beams where the transmission directions (angles) are different. At this time, whether to generate the processed element data of the element data obtained by the transmission of any ultrasonic beam (that is, whether to generate the processed element data of the sound ray in any direction) may be set by default according to the examination site, the type of probe, or the like, or may be selected by the operator.

In addition, the processed element data may be generated using both of the element data where the center elements are different and which is obtained by the transmission of parallel ultrasonic beams and the element data where the center elements are the same and which is obtained by the transmission of ultrasonic beams with different transmission directions.

As described above, the element data processor 22 sends the generated processed element data to the image generator 24 (the phasing addition section 38).

In the image generator 24 to which the processed element data is supplied, as described above, the reception data is generated by performing a reception focusing process by the phasing addition section 38 performing phasing addition on the processed element data and the detection processor 40 generates B mode image data by performing attenuation correction processing and envelope detection processing on the reception data.

In addition, in the image generator 24, the DSC 42 raster converts the B mode image data into image data corresponding to a normal television signal scanning method and performs predetermined processing such as gradation processing in the image processor 44.

The image processor 44 stores generated B mode image data in the image memory 46 and/or sends the generated B mode image data to the display controller 26 to display a B mode image of the subject on the monitor 28.

Next, more detailed description will be given of the method for selecting element data in the element data selector 47.

First, description will be given of the transmission frequency of the ultrasonic waves and the time difference between the (ghost) element data to be superimposed in the superimposition processor 49. Here, for the sake of simplicity in the following example, description will be given of superimposing two pieces of element data.

Figure 8A:
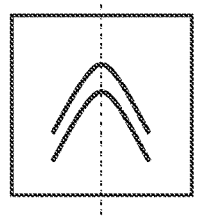
FIGS. 8A to 8C are conceptual diagrams for illustrating a relationship between a transmission frequency and a superimposition time difference.

As an example, FIG. 8A is a diagram in which, out of an element data group illustrated in FIG. 7D, the center element of the element data to the left of the element data in the middle is set as the element of interest and the element data on the left side thereof is superimposed thereon. That is, FIG. 8A illustrates a state in which delay time correction is performed on the element data on the left side and two pieces of element data are superimposed by shifting by one element in the azimuth direction.

As illustrated in FIG. 8A, because the element data of the element of interest in FIG. 8A is ghost element data, even when phase matching is performed by performing delay time correction and azimuth direction shifting, the element data do not overlap because the phases of each of the element data of the adjacent element and the element data of the element of interest do not match each other.

Figure 8B:
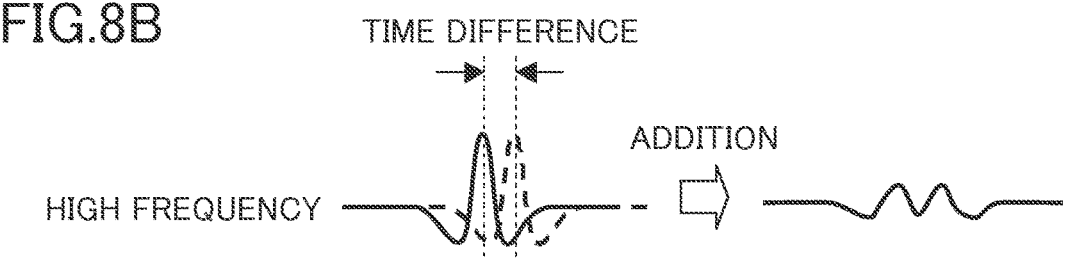
Figure 8C:
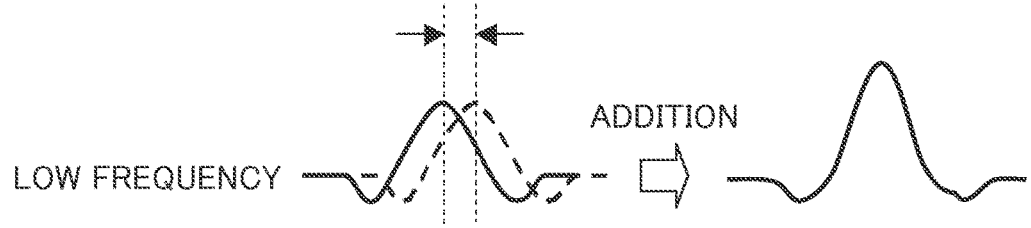

FIG. 8B and FIG. 8C are diagrams schematically illustrating the signal on a line (center element line) illustrated by a broken line in FIG. 8A. That is, in FIG. 8B and FIG. 8C, the horizontal axis is the time and the vertical axis is the signal strength.

Here, FIG. 8B illustrates a case where the half cycle of the ultrasonic waves is a transmission frequency of the same degree as the time difference in the reception time between element data to be superimposed. On the other hand, FIG. 8C illustrates a case where the half cycle of the ultrasonic waves is a transmission frequency which is longer than the time difference in the reception time between element data to be superimposed.

As illustrated in FIG. 8B, in a case where the half cycle of the ultrasonic waves is a transmission frequency of the same degree as the time difference in the reception time between element data to be superimposed, when addition processing (averaging processing) is carried out, the phases are canceled out because the phases are shifted each other and the signal is attenuated as illustrated on the right side in the diagram. That is, it is possible to eliminate the ghost signal.

On the other hand, as illustrated in FIG. 8C, in a case where the half cycle of the ultrasonic waves is a transmission frequency which is longer than the time difference in the reception time between element data to be superimposed, the signal is strengthened when the addition processing (averaging processing) is carried out as illustrated on the right side in the diagram because the phases are not sufficiently shifted between the signals. That is, it is not possible to eliminate the ghost signal.

Accordingly, in the element data selector 47, element data where the half cycle of the ultrasonic waves is the same degree as the time difference in the reception time between element data is selected as the element data to be superimposed. Accordingly, it is possible to appropriately eliminate the ghost signals when performing the multi-line processing.

Next, description will be given of the time difference in the reception time between the element data using FIG. 9.

Figure 9:
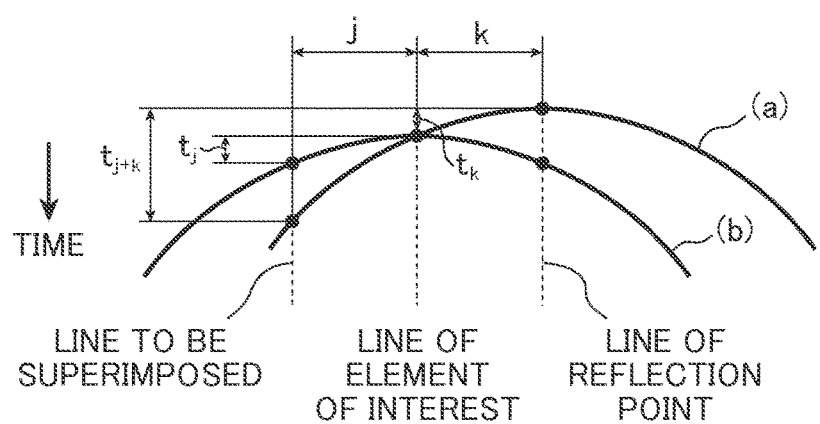
FIG. 9 is a conceptual diagram for illustrating a time difference in the reception time between element data.

In the same manner as FIG. 7B, the curved line denoted by (a) in FIG. 9 illustrates an example of the delay time in a case where an element located directly above a reflection point is the element of interest. In addition, in the same manner as FIG. 7E, the curved line denoted by (b) in FIG. 9 illustrates an example of the delay time in a case where an element at a position shifted from the reflection point is the element of interest.

The reflection point is located on a line where the element separated by k elements from the element of interest is set as the center element and element data acquired by setting the element separated by j elements from the element of interest as the center element is superimposed. When the delay time in a case of the center element being separated by x elements from the element of interest is set as $t_x$, from the curved line (a), the time difference in the reception time between the signal corresponding to the reflection point on the element data corresponding to the element of interest and the signal corresponding to the reflection point on the element data to be superimposed, before performing delay time correction is $t_{j+k}-t_k$. In a case where delay time correction is performed on the basis of the element of interest, correction with the delay time $t_j$ is performed with respect to the element data to be superimposed using the delay time indicated by the curved line (b). Accordingly, the time difference t in the reception time between the signal corresponding to the reflection point on the element data corresponding to the element of interest and the signal corresponding to the reflection point on the element data to be superimposed after performing delay time correction on the basis of the element of interest is $t=t_{j+k}-t_k-t_j$.

Next, using FIGS. 10A to 10C, description will be given of the method for selecting element data using the element data selector 47.

Similarly to FIG. 6C, FIG. 10A is a diagram schematically illustrating a signal on one line for each element data of an element data group where the center is true element data (element data obtained by transmission and reception where the positions of the reflection point and the center element match in the x direction) and which has ghost signals from the reflection point on both sides thereof, and illustrating a signal on a line corresponding to the center element in the true element data. In addition, in FIGS. 10A to 10C, the left and right direction in the diagrams represents time.

In addition, in FIG. 10A, the signal of the true element data in the center is set as Line 0 and the signals of the ghost element data on both sides thereof are set to Line ±1 to ±4 according to the element spacing from the Line 0.

As described above, when the superimposition is performed focusing on the element data of Line 0, processed element data where the signal from the reflection point is strengthened is obtained as the processed element data corresponding to Line 0.

Here, it is considered that the superimposition is performed focusing on the element data of Line 1. That is, it is considered that the superimposition is performed with respect to the ghost element data. In FIG. 10A, the curved line illustrated by a broken line is the delay time corresponding to the element data of Line 1 (corresponding to FIG. 7E). When performing delay time correction on the element data of Line −4 to Line 4 using this delay time, as illustrated in FIG. 10B, the delay time of each signal is corrected. Here, because the element data of the Line 1, which is of interest, is ghost element data, the reception times of each signal (element data) do not match even when the delay time correction is performed and the time difference t in the reception times is different for each according to the distance (intervals between the lines) from Line 1 which is of interest.

Here, as described above, the element data selector 47 selects element data of Line 2 and element data of Line −1 where the time difference t in the reception time is substantially the same as the half cycle of the transmitted ultrasonic waves (FIG. 10C).

The element data selector 47 supplies the element data which is of interest (in the illustrated example, the element data of Line 1) and the selected element data (in the illustrated example, the element data of Line 2 and the element data of Line −1) to the superimposition processor 49.

As described above, the superimposition processor 49 performs superimposition processing on the supplied element data and generates processed element data for the element data of interest (FIG. 10D). Here, because element data where the relationship of the time difference t is substantially the same as the half cycle of the ultrasonic waves is selected as the element data used in the superimposition processing, it is possible to eliminate the ghost signals because the phases of the ghost signals are shifted to cancel each other out as illustrated in FIG. 8B.

As described above, when correcting the data in the ultrasound diagnostic apparatus by superimposing a plurality of data (element data or reception data) obtained from each transmission according to the reception time or the position of the elements, the effect of the multi-line processing is increased as the number of data to be superimposed is increased and it is possible to suitably eliminate ghost signals. However, the signal processing takes time when the number of data to be superimposed is increased. Therefore, there is a problem in that this leads to a decrease in the frame rate. In addition, there is a problem in that a large capacity memory is necessary in order to temporarily hold (store) a large number of signals and costs are increased.

In contrast, when generating second element data corresponding to any of the first element data from a plurality of the first element data, that is, when performing the multi-line processing, the ultrasound diagnostic apparatus 10 of the present invention selects first element data to be superimposed according to the transmission frequency of the ultrasonic waves and generates second element data from the selected first element data.

Accordingly, even in a case where the superimposition is performed with a small number of data during the multi-line processing, because the peaks of the signals are shifted by a half cycle, the element data superimposed on each other are appropriately canceled out and the ghost signals can be eliminated. Accordingly, it is possible to obtain a high quality ultrasound image while preventing a decrease in the frame rate. In addition, because it is not necessary to hold large amounts of element data, it is not necessary to increase the capacity of the memory and it is possible to prevent increases in costs.

Here, in a case where the probe 12 is a probe transmitting an ultrasonic beam at a specific transmission frequency, when replacing the probe 12, the element data (line spacing) to be superimposed may be changed according to the transmission frequency of the probe 12.

Alternatively, in a case of the probe 12 being capable of changing the transmission frequency, when changing the transmission frequency, the element data (line spacing) to be superimposed may be changed according to the transmission frequency.

Next, with reference to examples, description will be given of the method for selecting the element data.

Example 1

As Example 1, a line separated by two lines from the reflection point was set as the line of interest and the time difference in the reception time between each of the elements was determined by simulation.

The probe 12 was set as a linear probe and the element spacing was set to 0.33 mm.

In addition, the transmission frequency was set to 5.5 MHz.

The focus point position was set to a depth of 2 mm.

The position of the reflection point was set to a depth of 4 mm.

The sound velocity was set to 1460 m/s.

Figure 11:
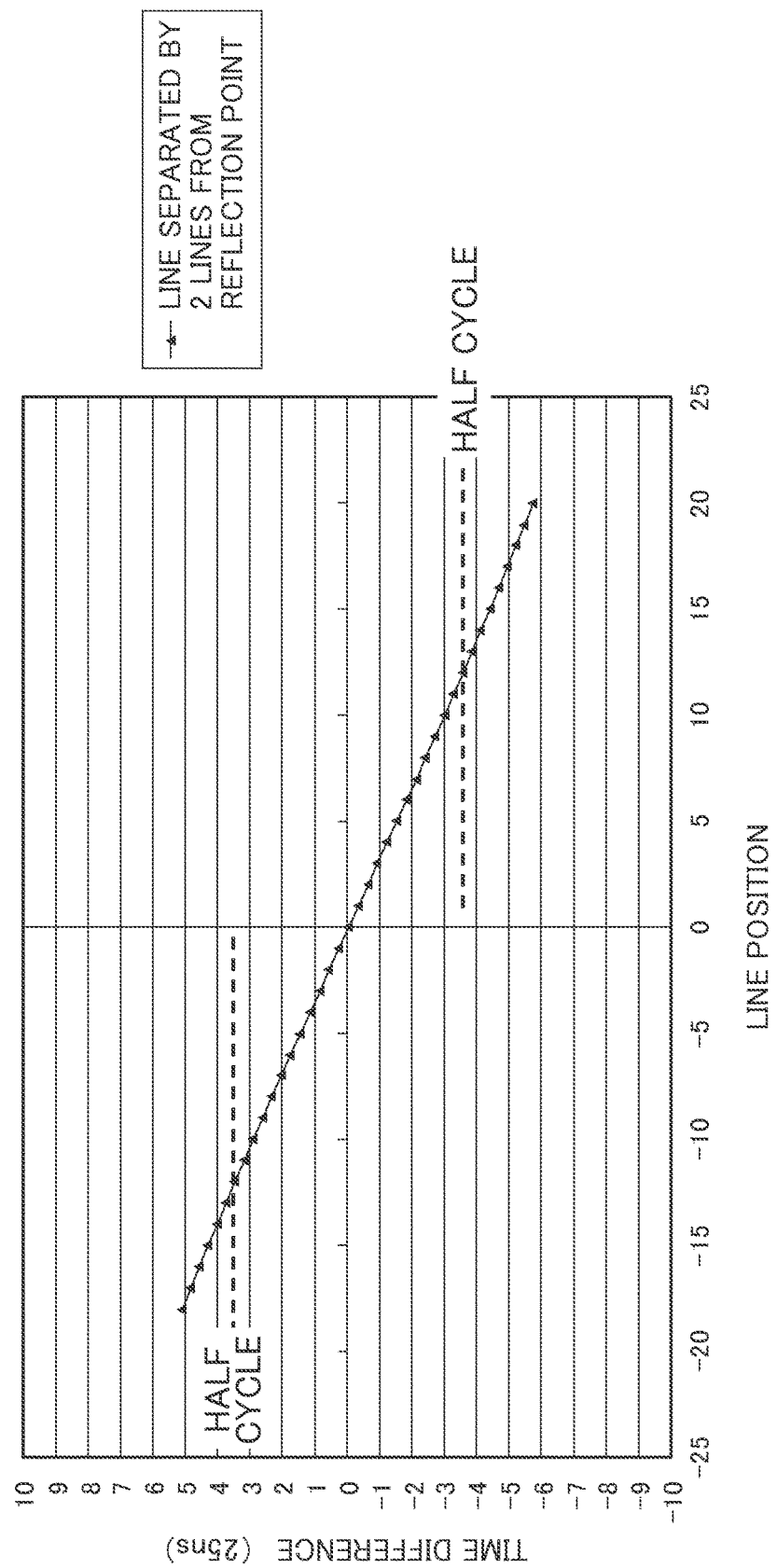
FIG. 11 is a graph illustrating a relationship between a line position and a time difference in the reception time.

The result of determining the time difference t in the reception time of the signal corresponding to the reflection point on the element data corresponding to each line (element) position with respect to the signal corresponding to the reflection point on the line of interest under these conditions is illustrated in FIG. 11.

Similarly to FIG. 10B, FIG. 11 is a graph representing a relationship between the line position and the time difference t in the reception time after performing delay time correction on the element data corresponding to each line on the basis of the line of interest. In FIG. 11, the vertical axis represents the time difference (25 ns) in the reception time between the line of interest and the surrounding lines and the horizontal axis is the line position. Here, regarding the horizontal axis, the sub-scanning direction of the ultrasonic waves is set as the positive direction and the origin is set to the position of the line of interest.

Here, because the transmission frequency is 5.5 MHz, the half cycle is approximately 90 ns (illustrated by the broken line in the diagram).

From FIG. 11, it is understood that the element data where the time difference in the reception time between the element data of the line of interest is a value closest to the half cycle of the ultrasonic waves is the element data corresponding to an element separated by +12 lines and the element data corresponding to an element separated by −12 lines.

Accordingly, the element data selector 47 reads out the element data of the line of interest and the element data corresponding to lines separated by 12 lines on both sides from the line of interest from the element data storage and supplies the read element data to the superimposition processor 49.

Here, the first embodiment is configured to select element data where the time difference in the reception time is a value closest to the half cycle of the ultrasonic waves; however, the present invention is not limited thereto, and may be configured to select element data where the time difference in the reception time is in a range of a ¼ cycle to a ¾ cycle of the ultrasonic waves. At that time, the present invention may be configured to select all of the element data in the range of a ¼ cycle to a ¾ cycle, or may be configured to select at least one from the element data in the range of a ¼ cycle to a ¾ cycle.

For example, because the ¼ cycle is approximately 45 ns and the ¾ cycle is approximately 135 ns in the embodiment illustrated in FIG. 11, from the diagram, it is possible to select element data corresponding to lines separated by +6 to +18 lines and element data corresponding to lines separated by −6 to −18 lines.

Here, as described above, the time difference in the reception time changes according to the positions of the reflection points. The positions of the reflection points of the ultrasound, for example, can be determined by analyzing the ultrasound image in the previous frame. Alternatively, determination is also possible by analyzing the acquired first element data or by temporarily generating an ultrasound image from the first element data and analyzing the image.

Accordingly, the time difference in the reception time may be determined by determining the positions of the reflection points with various known methods.

However, it is not always necessary to acquire information on the positions of the reflection points, and the present invention may be configured to select element data in the range of a ¼ cycle to a ¾ cycle with respect to each reflection point in a case where the reflection points are on different lines.

More detailed description will be given of this point using Example 2 in FIG. 12.

Example 2

Example 2 is the same as Example 1 except that the positions of the reflection points were positions separated by 1 to 5 lines from the line of interest, and the time difference in the reception time between each of the elements was determined by simulation.

Figure 12:
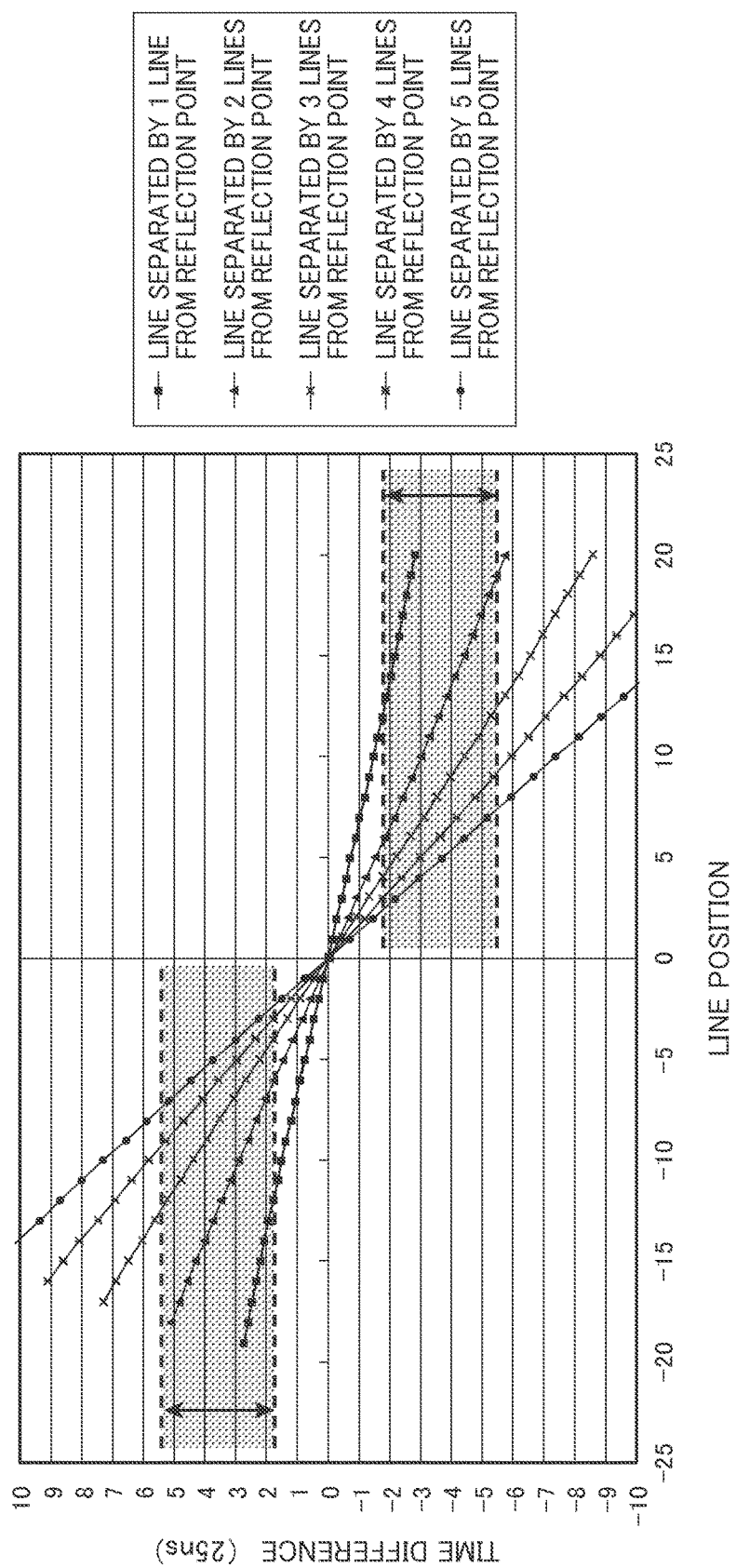
FIG. 12 is a graph illustrating a relationship between a line position and a time difference in the reception time.

The result of determining the time difference t in the reception time of the element data corresponding to each line position with respect to the line of interest for each reflection point position is illustrated in FIG. 12.

Similarly to FIG. 11, FIG. 12 is a graph representing a relationship between the line position and the time difference t in the reception time after performing delay time correction on the element data corresponding to each line on the basis of the line of interest. The vertical axis is the time difference (25 ns) in the reception time between the line of interest and the surrounding lines and the horizontal axis is the line position. Here, regarding the horizontal axis, the sub-scanning direction of the ultrasonic waves is set as the positive direction and the origin is set to the position of the line of interest. With respect to the line of interest, the time difference in a case where the reflection point is one line away is illustrated with square points, the time difference in a case where the reflection point is two lines away is illustrated with triangular points, the time difference in a case where the reflection point is three lines away is illustrated with crosses, the time difference in a case where the reflection point is four lines away is illustrated with asterisks, and the time difference in a case where the reflection point is five lines away is illustrated with circles. In addition, the range of the ¼ cycle to the ¾ cycle is illustrated with a broken line.

As can be seen from the diagram, the time difference in the reception time changes according to the relationship between the position of the line of interest and the position of the reflection point. In addition, the time difference in the reception time is increased as the position (line) of the reflection point is separated from the line of interest. Therefore, it is understood that the element data in the range of a ¼ cycle to a ¾ cycle are different according to the position of the reflection point.

Accordingly, in the example illustrated in FIG. 12, the element data selector 47 may select at least one from element data corresponding to lines separated by +12 to +20 lines and element data corresponding to lines separated by −12 to −19 lines corresponding to a case where the reflection point is one line away, may select at least one from element data corresponding to lines separated by +6 to +18 lines and element data corresponding to lines separated by −6 to −18 lines corresponding to a case where the reflection point is two lines away, may select at least one from element data corresponding to lines separated by +4 to +12 lines and element data corresponding to lines separated by −4 to −12 lines corresponding to a case where the reflection point is three lines away, may select at least one from element data corresponding to lines separated by +3 to +9 lines and element data corresponding to lines separated by −3 to −9 lines corresponding to a case where the reflection point is four lines away, or may select at least one from element data corresponding to lines separated by +3 to +7 lines and element data corresponding to lines separated by −3 to −7 lines corresponding to a case where the reflection point is five lines away.

Alternatively, element data in the range of a ¼ cycle to a ¾ cycle may be selected in a plurality of cases.

For example, in the illustrated example, because the element data corresponding to the lines separated by +6, +7, −6, and −7 lines is in the range of the ¼ cycle to the ¾ cycle as long as there is a reflection point 2 to 5 lines away, the element data selector 47 may select at least one of element data corresponding to lines separated by +6, +7, −6, and −7 lines.

Figure 13:
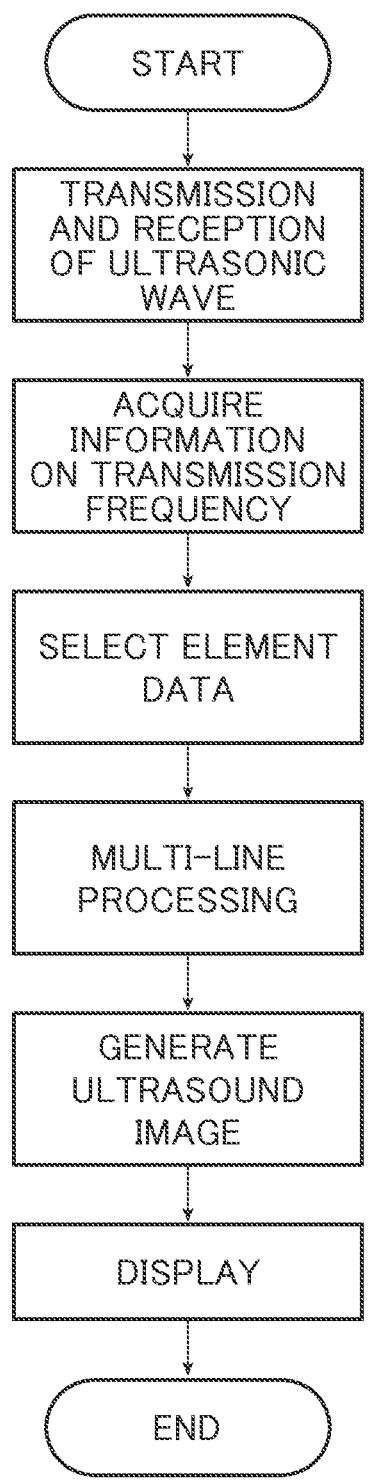
FIG. 13 is a flow chart for illustrating an operation of the ultrasound diagnostic apparatus illustrated in FIG. 1.

Detailed description will be given below of the signal processing method (the signal processing method of the present invention) in the ultrasound diagnostic apparatus 10 with reference to the flow chart illustrated in FIG. 13.

The program of the present invention is a program for causing a computer in the ultrasound diagnostic apparatus 10 to execute the signal processing method below.

In addition, the recording medium of the present invention is a recording medium on which the program described above is recorded. For example, the recording medium may be a memory which stores the program described above and which is attached to the controller or the like. Alternatively, the recording medium may be a memory medium (removable medium) configured to be inserted into and removed from an ultrasound inspection apparatus, such as a CD-ROM, or may be configured such that the program described above is read by a diagnostic apparatus via an interface corresponding to the removable medium.

In the ultrasound diagnostic apparatus 10, first, according to an instruction from the controller 30, in order to acquire the element data, the transmitter 14 transmits ultrasonic beams to the subject by driving (at a predetermined number of openings and opening positions) ultrasound transducers (elements) corresponding to the probe 12 (transducer array 36) at a set transmission frequency, receives ultrasonic echoes reflected from the subject using the ultrasound transducers (elements) and outputs an analog reception signal to the receiver 16.

The receiver 16 performs predetermined processing such as amplification on the analog reception signal and supplies the result to the A/D converter 18.

The A/D converter 18 analog-to-digital converts the analog reception signal supplied from the receiver 16 and sets the signal as element data constituted by a digital reception signal.

The element data is stored in the element data storage 20.

In addition, the frequency information acquiring unit 21 acquires information on the transmission frequency when the probe 12 transmits the ultrasonic beams and supplies the information to the element data processor 22.

As illustrated in FIG. 10B and FIG. 10C described above, the element data processor 22 firstly selects element data where the time difference in the reception time is the half cycle of the ultrasonic waves as the element data to be superimposed with the element of interest on the basis of information on the transmission frequency in the element data selector. Next, as illustrated in FIGS. 7A to 7H described above, the element data processor 22 performs delay time correction of the element data and azimuth direction shifting using the delay time calculated by the delay time calculator 48 with respect to the element data of interest and the selected element data, and generates processed element data of the element of interest by superimposing the selected element data on the element data of the element of interest. At this time, because the element data used in the superimposition is the element data where the time difference in the reception time is the half cycle of the ultrasonic waves, it is possible to prevent a decrease in the frame rate while appropriately eliminating the ghost signals with a small number of data.

The element data processor 22 generates a plurality of processed element data by performing the superimposition of the element data with respect to each of the element data corresponding to a predetermined plurality of lines. The element data processor 22 supplies the generated processed element data to the image generator 24. The image generator 24 generates ultrasound images (B mode image data) using the processed element data. At this time, it is possible to obtain a high quality ultrasound image because appropriately superimposed processed element data is used.

Here, the first embodiment is configured to use a predetermined sound velocity value set in advance as the ultrasound sound velocity. However, the present invention is not limited thereto and may be configured to have a sound velocity calculator which calculates the sound velocity and the element data (line spacing) to be superimposed may be changed according to the transmission frequency in a case where the sound velocity calculator calculates the sound velocity.

Here, the method for calculating the sound velocity of the sound velocity calculator is not particularly limited and various known sound velocity calculating methods used in ultrasound diagnostic apparatuses can be used.

In addition, the first embodiment is configured such that the multi-line processing is performed in the element data processor 22 using element data; however, the present invention is not limited thereto and may be configured to perform the multi-line processing on first reception data which is first element data subjected to phasing addition.

Figure 14:
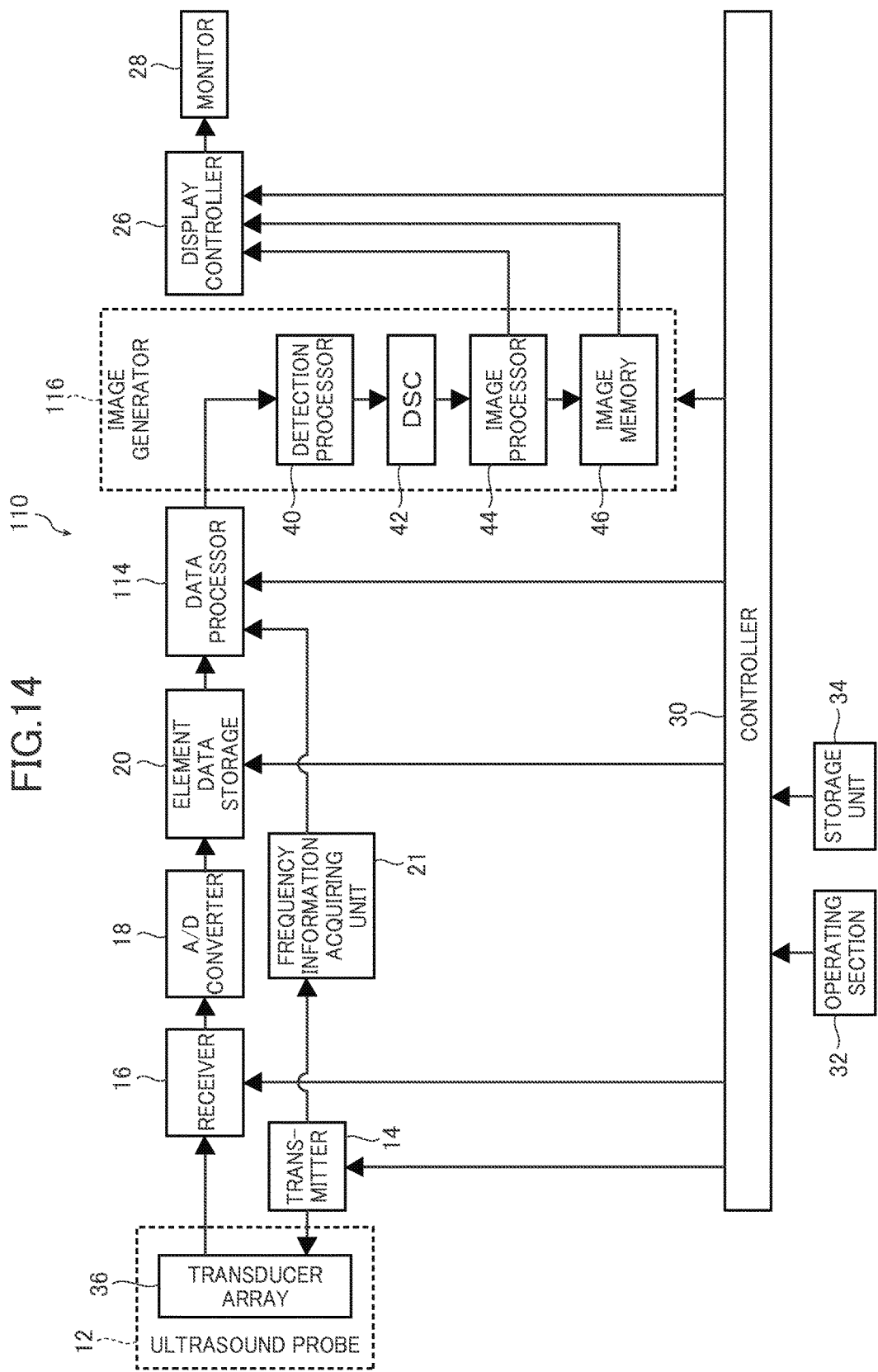
FIG. 14 is a block diagram conceptually illustrating another example of the configuration of the ultrasound diagnostic apparatus of the present invention.

FIG. 14 is a block diagram conceptually illustrating an example of an ultrasound diagnostic apparatus 110 which is the second embodiment of the present invention.

Here, because the ultrasound diagnostic apparatus 110 illustrated in FIG. 14 has the same configuration as the ultrasound diagnostic apparatus 10 illustrated in FIG. 1 except for having a data processor 114 instead of the element data processor 22 and having an image generator 116 instead of the image generator 24, the same reference numerals are given to the same constituent components and detailed description thereof will be omitted.

The ultrasound diagnostic apparatus 110 has the ultrasound probe 12, the transmitter 14 and the receiver 16 connected with the ultrasound probe 12, the A/D converter 18, the element data storage 20, the frequency information acquiring unit 21, the data processor 114, the image generator 116, the display controller 26, the monitor 28, the controller 30, the operating section 32, and the storage unit 34.

Figure 15:
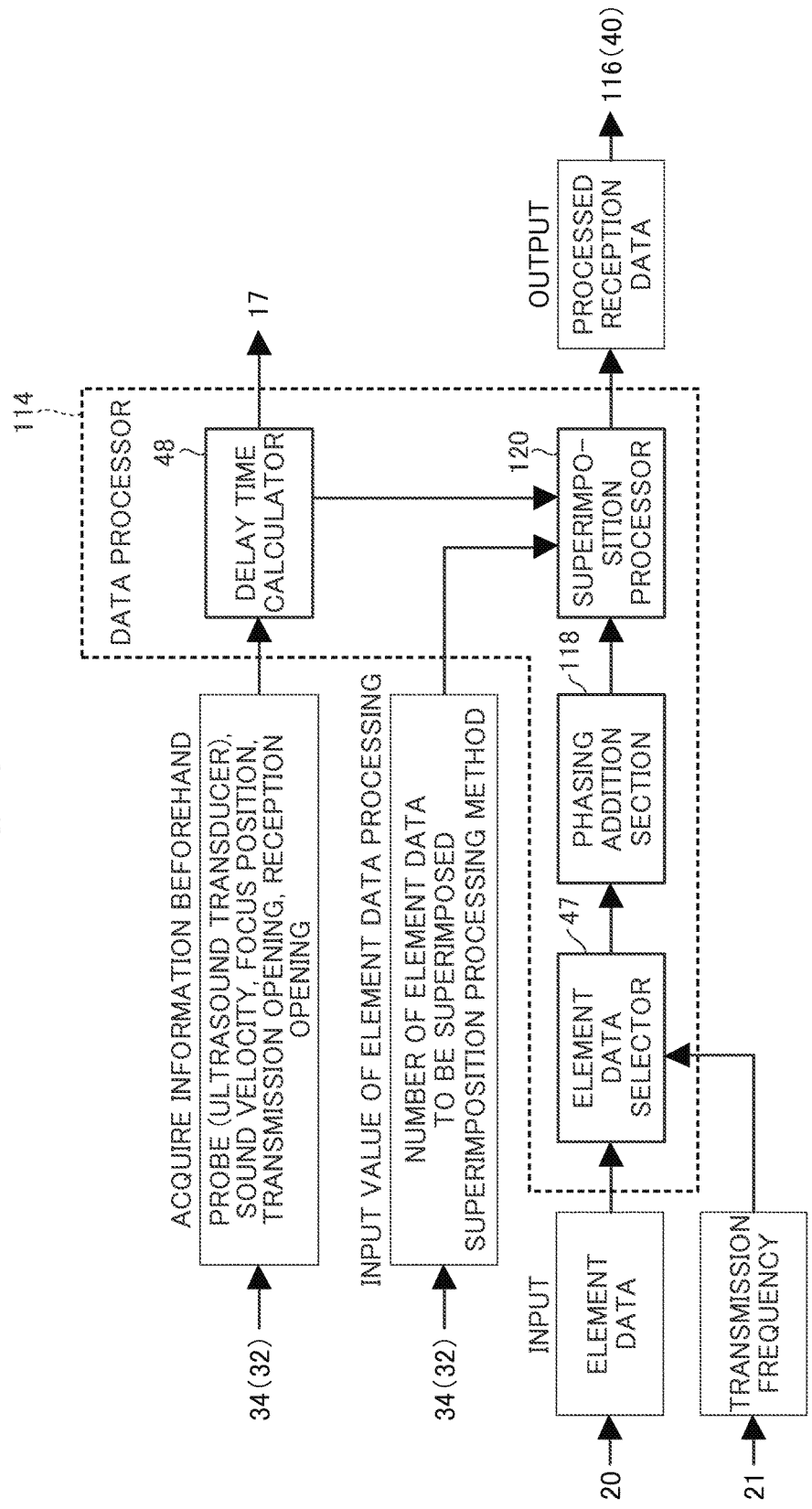
FIG. 15 is a block diagram conceptually illustrating an example of the configuration of a data processor of the ultrasound diagnostic apparatus illustrated in FIG. 14.

FIG. 15 is a block diagram conceptually illustrating the configuration of the data processor 114.

The data processor 114 has the element data selector 47, a phasing addition section 118, the delay time calculator 48, and a superimposition processor 120.

The phasing addition section 118 performs the reception focusing process by performing phasing addition on element data read out from the element data storage 20 by the element data selector 47, and generates first reception data.

Here, the phasing addition section 118 performs phasing addition for each of a plurality of element data to be superimposed by the superimposition processor 120 to be described below on the basis of the same element (line).

The superimposition processor 120 acquires the first reception data generated by the phasing addition section 118, and, on the basis of the delay time corresponding to each of the reception data calculated by the delay time calculator 48, generates processed (second) reception data by superimposing two or more of the first reception data in terms of the reception time, that is, by matching the times.

More detailed description will be given of the phasing addition section 118 and the superimposition processor 120 using FIG. 16 and FIGS. 17A to 17C.

Figure 16:
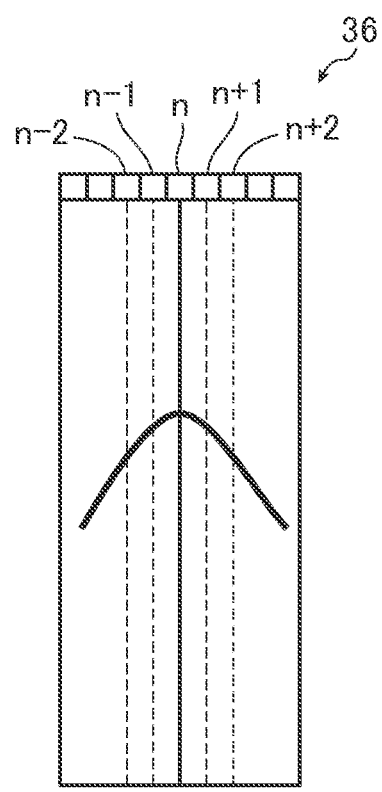
FIG. 16 is a diagram conceptually illustrating element data and elements.

FIG. 16 conceptually illustrates element data and the transducer array 36 at positions corresponding thereto.

The element data illustrated in FIG. 16 is element data obtained by performing the transmission and reception of ultrasonic waves with the n-th element set as the center element.

In the following description, for example, the reception data generated by performing phasing addition with respect to the n-th element data on the basis of the n−2th line is represented as n(n−2)th reception data. That is, the reception data obtained by performing phasing addition on the n-th element data on the basis of the i-th line is represented as n(i)th reception data.

FIGS. 17A to 17C are diagrams for illustrating phasing addition by the phasing addition section 118 and superimposition processing by the superimposition processor 120.

FIG. 17A illustrates each of n−2th element data, n−1th element data, and n-th element data.

As an example, a case of generating processed reception data corresponding to the n-th reception data using the n−2th, n−1th, and n-th reception data will be considered.

In a case where processed reception data corresponding to the n-th reception data is generated, the phasing addition section 118 performs phasing addition for each of the element data on the basis of the n-th element. That is, phasing addition is performed on each of the element data on the basis of the lines illustrated by solid lines in the diagram. The phasing addition generates first reception data (n−2(n)th reception data, n−1(n)th reception data, and n(n)th reception data) illustrated in FIG. 16B.

Next, for the first reception data generated by the phasing addition section 118, the superimposition processor 120 generates processed reception data corresponding to the n-th reception data as illustrated in FIG. 17C by superimposing each first reception data by matching the time on the basis of the delay time corresponding to each of the reception data calculated by the delay time calculator 48.

The data processor 114 supplies the processed reception data to the image generator 116.

The image generator 116 has a detection processor 40, a DSC 42, an image processor 44, and an image memory 46.

In the image generator 116, the detection processor 40 generates B mode image data by performing attenuation correction processing and envelope detection processing on the reception data. Furthermore, the DSC 42 raster converts the B mode image data into image data corresponding to a normal television signal scanning method and performs predetermined processing such as gradation processing in the image processor 44.

The image processor 44 stores generated B mode image data in the image memory 46 and/or sends the generated B mode image data to the display controller 26 to display a B mode image of the subject on the monitor 28.

The ultrasound diagnostic apparatus, the signal processing method, and the program of the present invention have been described above; however, the present invention is not limited to the examples described above and various improvements or modifications may be made within a range which does not depart from the gist of the present invention as a matter of course.

For example, in order to perform the multi-line processing without the element data storage 20 which stores element data for one image, the transmission and reception of the ultrasonic waves may be performed every time or a plurality of times as necessary corresponding to one element of interest.

What is claimed is:

1. An ultrasound diagnostic apparatus configured to inspect an inspection object using an ultrasonic beam, the apparatus comprising:
a probe having a plurality of elements arranged therein, the probe being configured to transmit the ultrasonic beam and receive an ultrasonic echo reflected by the inspection object, and to output an analog element signal according to the received ultrasonic echo;
a transmitter configured to cause the probe to transmit the ultrasonic beam a plurality of times using at least two of the plurality of elements as transmission elements so as to form a predetermined transmission focus point;
a receiver configured to receive analog element signals output by at least two of the plurality of elements that, as reception elements, have received an ultrasonic echo corresponding to individual transmission of the ultrasonic beam and to perform a predetermined process;
an analog-to-digital conversion circuit configured to analog-to-digital convert the analog element signals processed by the receiver into first element data formed by a digital element signal;
a data processor configured to generate second element data corresponding to any one of a plurality of first element data from the plurality of first element data;
a frequency information acquiring unit configured by a programmed computer that acquires information on a transmission frequency of the ultrasonic beam transmitted from the probe; and
an element data selector configured by a programmed computer that selects the plurality of first element data used for generating the second element data in the data processor on the basis of the information on the transmission frequency acquired by the frequency information acquiring unit;
wherein the data processor generates the second element data using the plurality of first element data selected by the element data selector.

2. The ultrasound diagnostic apparatus according to claim 1, wherein the data processor generates the second element data by superimposing the plurality of first element data according to reception times at which the reception elements have received the ultrasonic echo corresponding to individual transmission and positions of the reception elements.

3. The ultrasound diagnostic apparatus according to claim 1, wherein the element data selector selects at least one of the first element data where a time difference in reception time between the selected first element data when the data processor performs a superimposition is in a range of $1/4$ to $3/4$ of a cycle of the transmission frequency.

4. The ultrasound diagnostic apparatus according to claim 3, wherein the element data selector selects at least one of the first element data where a time difference in reception time between element data of interest is closest to a ½ cycle of the transmission frequency.

5. The ultrasound diagnostic apparatus according to claim 1, wherein the transmitter changes at least one of a center element and a transmission direction of the ultrasonic beam and causes the probe to transmit the ultrasonic beam a plurality of times.

6. The ultrasound diagnostic apparatus according to claim 5, wherein the data processor generates the second element data using at least one of the plurality of first element data obtained by transmission of the ultrasonic beam where the center element is different to each other and the plurality of first element data obtained by transmission of the ultrasonic beam where the transmission direction are different to each other.

7. The ultrasound diagnostic apparatus according to claim 1, wherein the data processor generates the second element data from the plurality of first element data obtained by transmission of the ultrasonic beam where transmission regions overlap.

8. The ultrasound diagnostic apparatus according to claim 1, further comprising a phasing addition section configured by a programmed computer that performs phasing addition on the first element data and generates first reception data;
  wherein the phasing addition section performs phasing addition on each of the plurality of first element data with a line corresponding to the same element set as the center, and generates a plurality of first reception data; and
  wherein the data processor generates second reception data corresponding to any one of the plurality of first reception data from the plurality of a first element data.

9. A signal processing method for an ultrasound diagnostic apparatus for inspecting an inspection object using a probe having a plurality of elements arranged therein, the probe transmitting an ultrasonic beam, receiving an ultrasonic echo reflected by the inspection object, and outputting an analog element signal according to the received ultrasonic echo, the method comprising:
  in the probe, a step of transmitting an ultrasonic beam a plurality of times so as to form a predetermined transmission focus point using at least two of the plurality of elements as transmission elements;
  a step of receiving an ultrasonic echo corresponding to individual transmission of the ultrasonic beam with at least two of the plurality of elements as reception elements and outputting an analog element signal;
  a step of analog-to-digital converting the analog element signal into first element data formed by a digital element signal;
  a step of performing data processing for generating second element data corresponding to any one of a plurality of first element data from the plurality of first element data;
  a step of acquiring information on a transmission frequency of the ultrasonic beam transmitted from the probe; and
  a step of selecting the plurality of first element data used for generating the second element data in the step of performing data processing on the basis of the information on the transmission frequency acquired by the step of acquiring information on the transmission frequency;
  wherein, in the step of performing data processing, the second element data is generated using the plurality of first element data selected by the step of selecting the plurality of first element data.

10. A non-transitory computer-readable recording medium having stored therein a program that causes a computer to execute a signal processing method for an ultrasound diagnostic apparatus for inspecting an inspection object using a probe having a plurality of elements arranged therein, the probe transmitting an ultrasonic beam, receiving an ultrasonic echo reflected by the inspection object, and outputting an analog element signal according to the received ultrasonic echo, the method comprising:
  in the probe, a step of transmitting an ultrasonic beam a plurality of times so as to form a predetermined transmission focus point using at least two of the plurality of elements as transmission elements;
  a step of receiving an ultrasonic echo corresponding to individual transmission of the ultrasonic beam with at least two of the plurality of elements as reception elements and outputting an analog element signal;
  a step of analog-to-digital converting the analog element signal into first element data formed by a digital element signal;
  a step of performing data processing for generating second element data corresponding to any one of a plurality of first element data from the plurality of first element data;
  a step of acquiring information on a transmission frequency of the ultrasonic beam transmitted from the probe; and
  a step of selecting the plurality of first element data used for generating the second element data in the step of performing data processing on the basis of the information on the transmission frequency acquired by the step of acquiring information on the transmission frequency;
  wherein, in the step of performing data processing, the second element data is generated using the plurality of first element data selected by the step of selecting the plurality of first element data.

* * * * *